US011352631B2

(12) United States Patent
Lee et al.

(10) Patent No.: US 11,352,631 B2
(45) Date of Patent: Jun. 7, 2022

(54) TARGETED DISRUPTION OF THE T CELL RECEPTOR

(71) Applicant: Sangamo BioSciences, Inc., Richmond, CA (US)

(72) Inventors: Gary K. Lee, Richmond, CA (US); David Paschon, Richmond, CA (US); Lei Zhang, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 161 days.

(21) Appl. No.: 15/380,643

(22) Filed: Dec. 15, 2016

(65) Prior Publication Data

US 2017/0211075 A1    Jul. 27, 2017

Related U.S. Application Data

(60) Provisional application No. 62/269,365, filed on Dec. 18, 2015, provisional application No. 62/306,500, filed on Mar. 10, 2016.

(51) Int. Cl.
| | |
|---|---|
| *C12N 15/62* | (2006.01) |
| *C12N 15/63* | (2006.01) |
| *A61K 48/00* | (2006.01) |
| *C12N 15/52* | (2006.01) |
| *C12N 5/073* | (2010.01) |
| *C12N 5/0735* | (2010.01) |
| *C12N 5/0783* | (2010.01) |
| *C12N 5/074* | (2010.01) |
| *C12N 9/16* | (2006.01) |

(52) U.S. Cl.
CPC ............ *C12N 15/52* (2013.01); *C12N 5/0603* (2013.01); *C12N 5/0606* (2013.01); *C12N 5/0636* (2013.01); *C12N 5/0696* (2013.01); *C12N 9/16* (2013.01); *C12N 15/62* (2013.01)

(58) Field of Classification Search
None
See application file for complete search history.

(56) References Cited

U.S. PATENT DOCUMENTS

| | | | |
|---|---|---|---|
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox et al. | |
| 6,599,692 B1 | 7/2003 | Case et al. | |
| 6,607,882 B1 | 8/2003 | Cox et al. | |
| 6,689,558 B2 | 2/2004 | Case et al. | |
| 6,794,136 B1 | 9/2004 | Eisenberg et al. | |
| 6,824,978 B1 | 11/2004 | Cox et al. | |
| 6,903,185 B2 | 6/2005 | Kim et al. | |
| 6,933,113 B2 | 8/2005 | Case et al. | |
| 6,979,539 B2 | 12/2005 | Cox et al. | |
| 7,013,219 B2 | 3/2006 | Case et al. | |
| 7,030,215 B2 | 4/2006 | Liu et al. | |
| 7,053,264 B2 | 5/2006 | Wolffe | |
| 7,067,317 B2 | 6/2006 | Rebar et al. | |
| 7,070,934 B2 | 7/2006 | Cox et al. | |
| 7,153,949 B2 | 12/2006 | Kim et al. | |
| 7,163,824 B2 | 1/2007 | Cox et al. | |
| 7,217,509 B2 | 5/2007 | Wolffe et al. | |
| 7,253,273 B2 | 8/2007 | Collingwood | |
| 7,262,054 B2 | 8/2007 | Jamieson et al. | |
| 7,361,635 B2 | 4/2008 | Miller et al. | |
| 7,785,792 B2 | 8/2010 | Wolffe et al. | |
| 7,888,121 B2 | 2/2011 | Urnov et al. | |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Dotti et al., Blood, 2009, 114: 1457-1458.*
Minczuk et al., Nucl. Acids Res., 2008, 36: 3926-3938.*
Wefers et al., Nature Protocols, 2013, 8: 2355-2379.*
Poirot et al., Cancer Res., online Jul. 16, 2015, 75: 3853-3864.*
Jinek et al., Science, 2012, 337: 816-821.*
Provasi et al., Nature Medicine, 2012, 18: 807-815.*
Perez et al., Nat. Biotechnol., 2008, 26: 808-816.*

(Continued)

*Primary Examiner* — Ileana Popa
(74) *Attorney, Agent, or Firm* — Foley & Lardner LLP

(57) ABSTRACT

Disclosed herein are methods and compositions for inactivating TCR genes, using engineered nucleases comprising at least one DNA binding domain and a cleavage domain or cleavage half-domain in conditions able to preserve cell viability. Polynucleotides encoding nucleases, vectors comprising polynucleotides encoding nucleases and cells comprising polynucleotides encoding nucleases and/or cells comprising nucleases are also provided. Disclosed herein are also methods and compositions for expressing a functional exogenous TCR in the absence of endogenous TCR expression in T lymphocytes, including lymphocytes with a central memory phenotype. Polynucleotides encoding exogenous TCR, vectors comprising polynucleotides encoding exogenous TCR and cells comprising polynucleotides encoding exogenous TCR and/or cells comprising exogenous TCR are also provided.

11 Claims, 8 Drawing Sheets

Specification includes a Sequence Listing.

(56) References Cited

U.S. PATENT DOCUMENTS

| | | | |
|---|---|---|---|
| 7,914,796 B2 | 3/2011 | Miller et al. |
| 7,923,542 B2 | 4/2011 | Wolffe et al. |
| 7,951,925 B2 | 5/2011 | Ando et al. |
| 7,972,854 B2 | 7/2011 | Miller et al. |
| 8,034,598 B2 | 10/2011 | Miller |
| 8,071,370 B2 | 12/2011 | Wolffe et al. |
| 8,110,379 B2 | 2/2012 | DeKelver et al. |
| 8,409,861 B2 | 4/2013 | Guschin et al. |
| 8,563,314 B2 | 10/2013 | Gregory et al. |
| 8,586,526 B2 | 11/2013 | Gregory et al. |
| 8,623,618 B2 | 1/2014 | Doyon et al. |
| 8,697,359 B1 | 4/2014 | Zhang |
| 8,703,489 B2 | 4/2014 | Wang |
| 8,771,985 B2 | 7/2014 | Cui et al. |
| 8,772,453 B2 | 7/2014 | Paschon et al. |
| 8,945,868 B2 | 2/2015 | Collingwood et al. |
| 8,956,828 B2 | 2/2015 | Bonini et al. |
| 9,005,973 B2 | 4/2015 | Cost et al. |
| 9,045,763 B2 | 6/2015 | DeKelver et al. |
| 9,200,266 B2 | 12/2015 | Wang |
| 9,255,250 B2 | 2/2016 | Gregory et al. |
| 9,458,205 B2 | 10/2016 | Gregory et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0267061 A1 | 12/2005 | Martin |
| 2006/0063231 A1 | 3/2006 | Li et al. |
| 2007/0218528 A1 | 9/2007 | Miller |
| 2008/0131962 A1 | 6/2008 | Miller |
| 2008/0159996 A1 | 7/2008 | Ando et al. |
| 2009/0068164 A1 | 3/2009 | Segal et al. |
| 2009/0136465 A1 | 5/2009 | Merenick et al. |
| 2010/0003756 A1 | 1/2010 | Collingwood et al. |
| 2010/0218264 A1 | 8/2010 | Cui et al. |
| 2011/0136895 A1* | 6/2011 | Gregory .............. C12N 9/22 514/44 R |
| 2011/0145940 A1 | 6/2011 | Voytas et al. |
| 2011/0158957 A1* | 6/2011 | Bonini .............. C12N 9/22 424/93.7 |
| 2011/0201055 A1 | 8/2011 | Doyon et al. |
| 2011/0265198 A1 | 10/2011 | Gregory et al. |
| 2011/0301073 A1 | 12/2011 | Gregory et al. |
| 2012/0017290 A1 | 1/2012 | Cui et al. |
| 2012/0060230 A1 | 3/2012 | Collingwood et al. |
| 2012/0195936 A1 | 8/2012 | Rudolph et al. |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2013/0315884 A1* | 11/2013 | Galetto ............ C07K 14/70517 424/93.71 |
| 2014/0120622 A1 | 5/2014 | Gregory et al. |
| 2014/0301990 A1 | 10/2014 | Gregory et al. |
| 2015/0056705 A1 | 2/2015 | Conway et al. |
| 2015/0132269 A1 | 5/2015 | Orkin et al. |
| 2015/0159172 A1 | 6/2015 | Miller et al. |
| 2015/0164954 A1 | 6/2015 | Bonini et al. |
| 2016/0272999 A1* | 9/2016 | Duchateau .......... C12N 5/0636 |
| 2016/0326548 A1 | 11/2016 | Cost |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/099084 A2 | 12/2002 |
| WO | WO 03/016496 A2 | 2/2003 |
| WO | WO-2003/089603 | 10/2003 |
| WO | WO 10/079430 A1 | 7/2010 |
| WO | WO-2012/027611 | 3/2012 |
| WO | WO 14/059173 A2 | 4/2014 |
| WO | 2014/184741 A1 | 11/2014 |
| WO | WO-2014/191128 | 12/2014 |
| WO | 2015136001 A1 | 9/2015 |

OTHER PUBLICATIONS

Beerli, et al., "Engineering Polydactyl Zinc-Finger Transcription Factors," *Nature Biotechnology* 20:135-141 (2002).

Beurdeley, et al., "Compact Designer Talens for Efficient Genome Engineering," *Nat Comm* 4:1762 doi: 10.1038/ncomms2782 (2013).

Boch, et al., "Breaking the Code of DNA Binding Specificity of Tal-Type III Effectors," *Science* 326:1509-1512 (2009).

Boissel, et al., "Megatals: a Rare-Cleaving Nuclease Architecture for Therapeutic Genome Engineering," *Nucleic Acids Research* 42:4:2591-2601 (2013) doi: 10.1093/nar/gkt1224.

Bonas, et al., "Genetic and Structural Characterization of the Avirulence Gene avrBs3 from *Xanthomonas campestris* pv. *vesicatoria*," *Molecular and General Genetics* 218:127-136 (1989).

Brady, et al., "Antigen Receptor Allelic Exclusion: an Update and Reappraisal," *The Journal of Immunology* 185:3801-3808 (2010).

Chicaybam, et al.,"Chimeric Antigen Receptors in Cancer Immuno-Gene Therapy: Current Status and Future Directions," *International Reviews of Immunology* 30:294-311 (2011).

Choo, et al., "Advances in Zinc Finger Engineering," *Curr. Opin. Struct. Biol.* 10:411-416 (2000).

Guillinger, et al., "Fusion of Catalytically Inactive Cas9 to FokI Nuclease Improves the Specificity of Genome Modification," *Nature Biotechnology* 32(6): 577-582 (2014).

Guo, et al., "Directed Evolution of an Enhanced and Highly Efficient FokI Cleavage Domain for Zinc Finger Nucleases," *Journal of Molecular Biology* 400(1):96-107 (2010).

Haft, et al., "A Guild Of 45 CRISPR-Associated (Cas) Protein Families and Multiple CRISPR/Cas Subtypes Exist in Prokaryotic Genomes," *PLoS Computational Biology* 1(6):e60 (2005).

Heuer, et al., "Repeat Domain Diversity Of avrBs3-LIKE Genes in Ralstonia solanacearum Strains and Association With Host Preferences in the Field," *Applied and Environmental Microbiology* 73(13):4379-4384 (2007).

Isalan et al., "A Rapid, Generally Applicable Method To Engineer Zinc Fingers Illustrated By Targeting the HIV-1 Promoter," *Nature Biotechnology* 19:656-660 (2001).

Jansen, et al., "Identification of Genes That Are Associated With DNA Repeats in Prokaryotes," *Molecular Microbiology* 43(6):1565-1575 (2002).

Kalos, et al., "T Cells With Chimeric Antigen Receptors Have Potent Antitumor Effects and Can Establish Memory in Patients With Advanced Leukemia," *Science Translational Medicine* 3:95ra73 (2011).

Kariko, et al., "HPLC Purification Eliminates Immune Activation and Improves Translation of Nucleoside-Modified, Protein-Encoding mRNA," *Nucleic Acids Research* 39(21):e142 (2011).

Kay, et al., "A Bacterial Effector Acts as a Plant Transcription Factor and Induces a Cell Size Regulator," *Science* 318:648-651 (2007).

Kollmannsperger, et al., "Live-Cell Protein Labelling With Nanometre Precision By Cell Squeezing," *Nature Communications* 7:10372 (2016).

Kormann, et al., Expression of Therapeutic Proteins After Delivry of Chemically Modified mRNA in Mice, *Nature Biotechnology* 29(2):154-157 (2011).

Lombardo, et al., Gene Editing in Human Stem Cells Using Zinc Finger Nucleases and Integrase-Defective Lentiviral Vector Delivery, *Nature Biotechnology* 25(11): 1298-1306 (2007).

Makarova, et al., "A DNA Repair System Specific for Thermophilic Archaea and Bacteria Predicted By Genomic Context Analysis," *Nucleic Acids Research* 30:482-496 (2002).

Makarova, et al., "A Putative RNA-Interference-Based Immune System in Prokaryotes: Computational Analysis of the Predicted Enzymatic Machinery, Functional Analogies With Eukaryotic RNAi, and Hypothetical Mechanisms of Action," *Biol. Direct* 1:7 (2006).

(56) References Cited

OTHER PUBLICATIONS

McCaffrey, et al., "CRISPR-CAS9 D10A Nickase Target-Specific Fluorescent Labeling of Double Strand DNA for Whole Genome Mapping and Structural Variation Analysis," *Nucleic Acids Research* 44(2):e11 (2016) doi: 10.1093/nar/gkv878. ePub Oct. 19, 2015.
Moscou, et al., "A Small Cipher Governs DNA Recognition By TAL Effectors," *Science* 326:1501 (2009).
Olovnikov, et al., "Bacterial Argonaute Samples the Transcriptome To Identify Foreign DNA," *Molecular Cell* 51:594-605 (2013).
Pabo, et al., "Design and Selection of Novel CYS2-HIS2 Zinc Finger Proteins," *Ann. Rev. Biochem.* 70:313-340 (2001).
Ran, et al., "In vivo Genome Editing Using *Staphylococcus aureus* Cas9," *Nature* 520:186 (2015).
Rosenberg, et al., "Durable Complete Responses in Heavily Pretreated Patients With Metastatic Melanoma Using T-Cell Transfer Immunotherapy," *Clinical Cancer Research* 17(3):4550-4557 (2011).
Schornack, et al., "Gene-For-Gene-Mediated Recognition of Nuclear-Targeted AvrBs3-like Bacterial Effector Proteins," *Journal of Plant Physiology* 163(3):256-272 (2006).
Scott, et al., "Antibody Therpay of Cancer," *Nature Reviews Cancer* 12:278 (2012).
Segal, et al., "Custom DNA-Binding Proteins Come of Age: Polydactyl Zinc-Finger Proteins," *Curr. Opin. Biotechnol.* 12:632-637 (2001).
Sheng, et al., "Structure-Based Cleavage Mechanism of *Thermus thermophilus* Argonaute DNA Guide Strand-Mediated DNA Target Cleavage," *Proc. Natl. Acad. Sci. U.S.A.* 111(2):652-657 (2014).
Smietanski, et al., "Structural Analysis of Human 2'-O-Ribose Methyltransferases Involved in mRNA Cap Structure Formation," *Nature Communications* 5:3004 (2014).
Swarts, et al., "DNA-Guided DNA Interference By a Prokaryotic Argonaute" *Nature* 507(7491):258-261 (2014).
Urnov, et al., "Highly Efficient Endogenous Human Gene Correction Using Designed Zinc-Finger Nucleases," *Nature* 435(7042):646-651 (2005).
Vogel, "A Bacterial Seek-and-Destroy System for Foreign DNA," *Science* 344(6187):972-973 (2014).
Yuan, et al., "Crystal Structure of *A. aeolicus* Argonaute, a Site-Specific DNA-Guided Endoribonuclease, Provides Insights Into Risc-Mediated mRNA Cleavage," *Molecular Cell* 19:405-419 (2005).
Fang, et al., "Zinc Finger B-Box Domain Containing Protein 1 [Crassostrea Gigas]," National Center for Biotechnology Information, GenBank: EKC35827.1 (2011).
Meyer, et al., "Zing Finger Protein [Oryctes Borbonicus]," National Center for Biotechnology Information, GenBank: KR84692.1 (2015).
Polic, et al. "HowT cells deal with induced TCR ablation," PNAS 98: 8744-8749 (2001).

\* cited by examiner

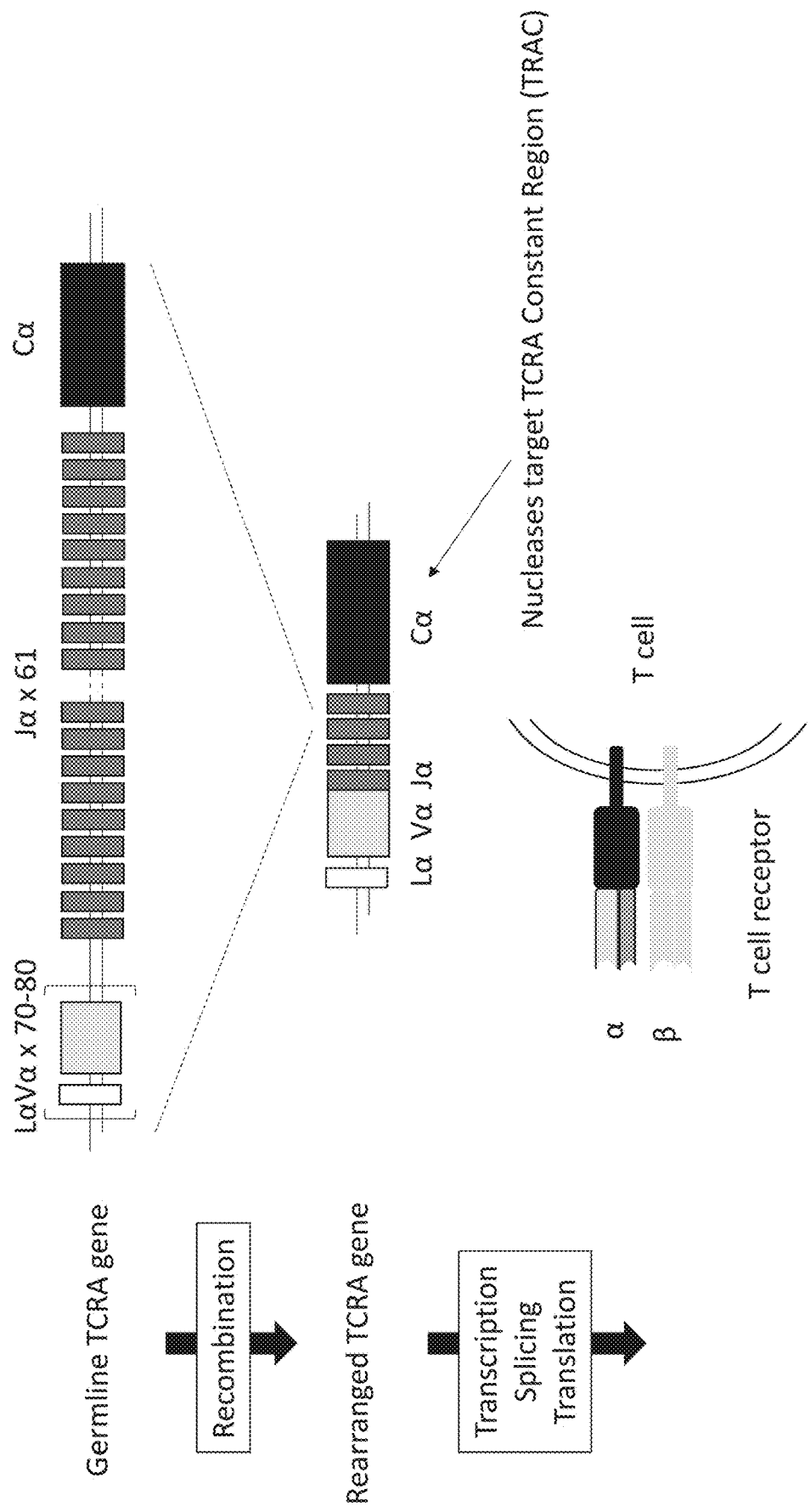

Figure 1B

Exon c1

1 aTATCCAGAACCCTGACCCTGCCGTGTACCAGCTGAGAGACTCTAAATCCAGTGACAAGTCTGTCTGCCTATTCACCGATTTGATTCTCAAACAAATGT

101 GTCACAAAGTAAGGATTCTGATGTGTATATCACAGACAAAACTGTGTCTAGACATGAGGTCTAtGGACTTtCAAGAGCTAtCAACAGTtCTGTGGCCTGGAGCAAC
                                                                    F              A  B

201 AAATCTGACTTTGCAATGCAAACGCCTTTCAACAACACAGCAGCATTATTCCAGAAGAGACACCTTCTCCCCAGCCCA...

Exon c2

2101 ...GAAAGTTCCTGTGATGTCAAGCTGGTCGAGAAAAGCTtTTGAAACAG...
                                                      E

Exon c3

3021 ...ATACGAACCTAAACTTTCAAAACCTGTCAGTGATTGGGTTCCGAATCTtCTtCCTGAAAGTGGCC
                                                  G  D
                                                 Arg      lys

3121 GGGTTTAATCTGCTCATGACGCTGCGGCTGTGGTCCAGCTGAG...
                         *

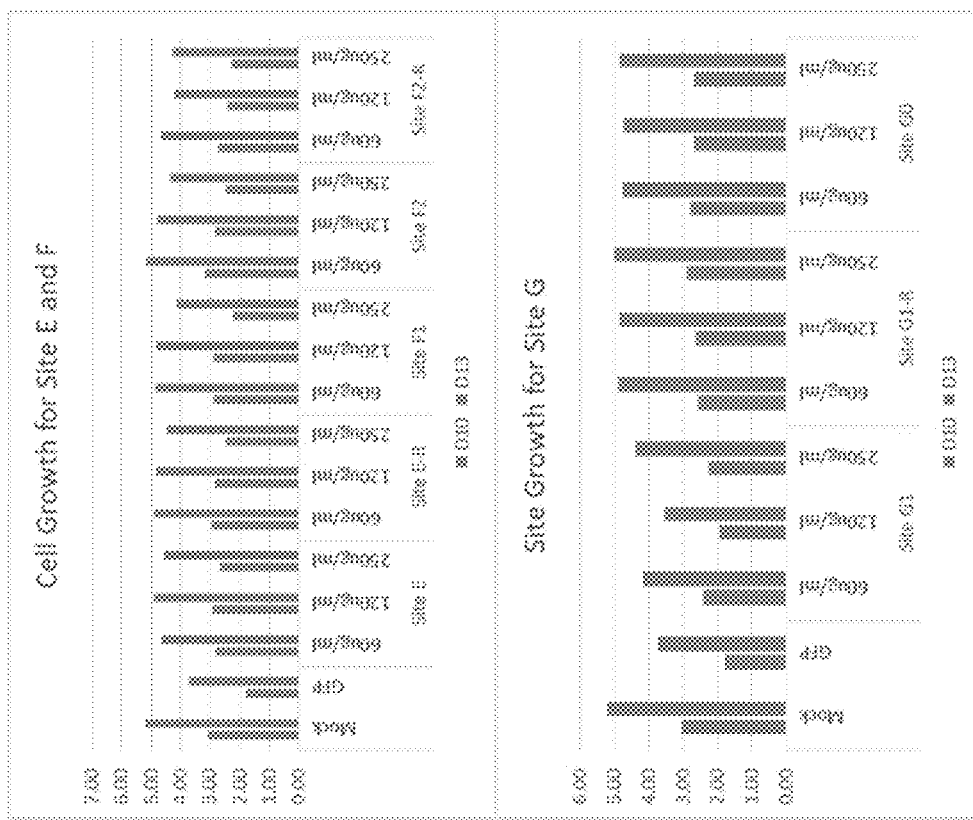
Figure 5A
Figure 5B
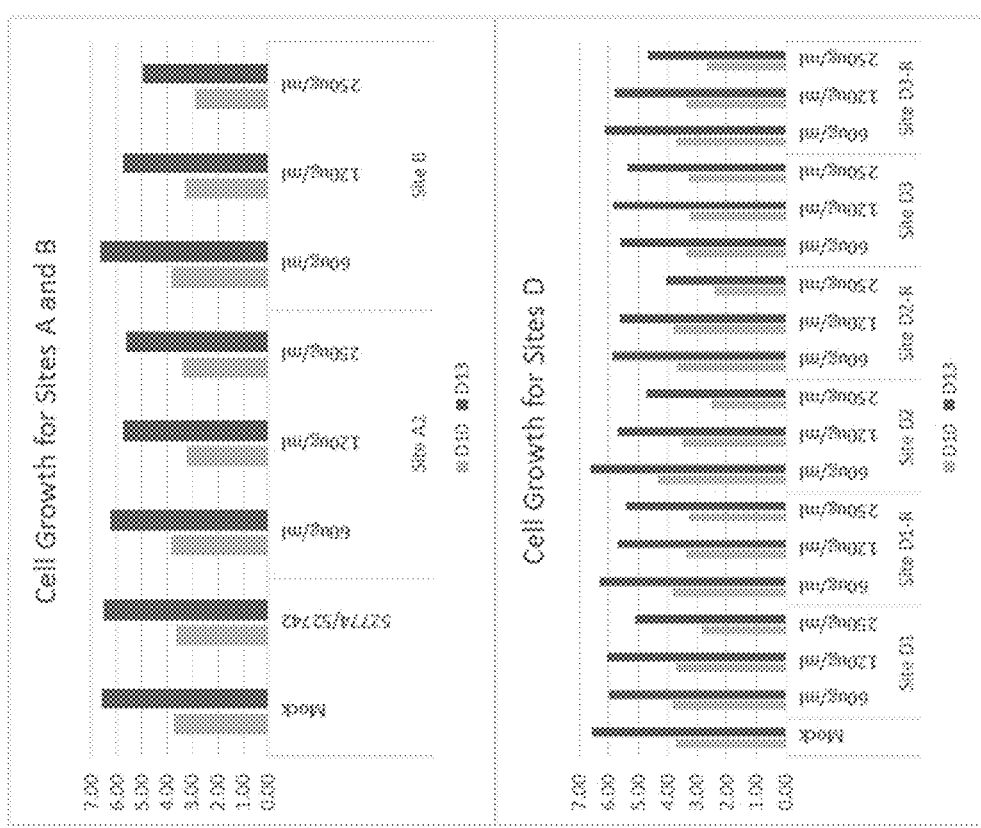
Figure 5C
Figure 5D
Total cell doublings

Figure 6

| ug/mL | TRAC- | B2M- | FACS DOUBLE- | D10 Total GFP+ | DOUBLE-GFP+ |
|---|---|---|---|---|---|
| sham | 0.5 | 0.1 | 0.0 | 0.0 | 0.0 |
| TRAC/B2M KO only | 85.0 | 83.6 | 80.0 | 0.0 | 0.0 |
| TRAC/B2M KO + 1E5vg/cell TRAC locus AAV donor | 91.9 | 92.7 | 89.3 | 80.8 | 83.0 |
| TRAC/B2M KO + 3E4vg/cell TRAC locus AAV donor | 91.2 | 93.4 | 89.1 | 71.9 | 74.3 |
| TRAC/B2M KO + 1E5vg/cell B2M locus AAV donor | 88.2 | 90.5 | 86.4 | 54.9 | 59.6 |
| TRAC/B2M KO + 3E4vg/cell B2M locus AAV donor | 89.8 | 92.2 | 87.9 | 43.2 | 46.7 |

SEQUENCE LISTING

<160> NUMBER OF SEQ ID NOS: 125

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Leu Val Lys Ser
1               5

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Gly Thr Pro His Glu Val Gly Val Tyr Thr Leu
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Gly Ala Ile Arg Cys His Asp Glu Phe Trp Phe
1               5                   10

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
ttgctcttga agtccataga cctcatgt                                              28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtgctgtggc ctggagcaac aaatctga                                              28

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctgttgctct tgaagtccat agacctca                                              28

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctgtggcctg gagcaacaaa tctgactt                                              28

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aggattcgga acccaatcac tg                                                    22

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctcctgaaag tggccgggtt taatctgc                                              28

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aggattcgga acccaatcac tgacaggt                                              28

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tcaagctggt cgagaaaagc tttgaaac                                              28

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aacaggtaag acagggtct agcctggg                                               28

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctgtgctaga catgaggtct atggactt                                              28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ttcaagagca acagtgctgt ggcctgga                                              28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cctgtcagtg attgggttcc gaatcctc                                              28

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 20
tcctcctgaa agtggccggg tttaatct                                          28

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ctgtgctaga catgaggtct atg                                               23

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Arg Ser Asn Leu Ser Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Lys Val Thr Leu Ala Ala
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Arg Ser Ala Leu Ser Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Ser Gly Asn Leu Thr Arg
1               5

<210> SEQ ID NO 26
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 26

Tyr Arg Ser Ser Leu Lys Glu
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Gln Asn Val Leu Ile Asn
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Asn Ala Thr Arg Thr Lys
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Ser Gly His Leu Ala Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asn Arg Tyr Asp Leu Met Thr
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ser Asp Ser Leu Leu Arg
1               5
```

```
<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Ser Ser Asp Leu Thr Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Arg Ser Ala Leu Ala Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ser Gly Asn Leu Ala Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

His Arg Ser Thr Leu Gln Gly
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ser Gly Asp Leu Thr Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37
```

```
Thr Ser Gly Ser Leu Thr Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln His Gln Val Leu Val Arg
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ser Gly His Leu Ser Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Arg Ser Asp Leu Ser Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ser Asp Ala Leu Ala Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Gln Ser Asn Leu Arg Ala
1               5

<210> SEQ ID NO 43
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 43

Thr Ser Ser Asn Arg Lys Thr
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Ser Ser Thr Arg Lys Thr
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Ser Asp Asp Leu Ser Glu
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Asn Ser Asn Arg Lys Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ser Asp His Leu Ser Thr
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Arg Ser His Leu Ala Arg
1               5
```

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Lys Gln His Leu Asn Glu
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

His Arg Thr Ser Leu Thr Asp
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Gln Gln Thr Leu Ala Asp
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Arg Glu Asp Leu Ile Thr
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Ser Ser Asn Leu Ser Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 54

His Asn Ser Ser Leu Lys Asp
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Asn His His Leu Gln Gln
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

His Lys Thr Ser Leu Lys Asp
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Ser Ser Asp Leu Ser Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Ser Gly Asn Arg Thr Thr
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Ser Ala Asn Leu Ala Arg
1               5

<210> SEQ ID NO 60
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 60

Arg Ser Asp Val Leu Ser Glu
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys His Ser Thr Arg Arg Val
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Met His Gln Arg Val Glu
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Ser Gly His Leu Ser Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ser Asp His Leu Thr Gln
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asp Ser Ala Asn Leu Ser Arg
1               5
```

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Ser Gly Ser Leu Thr Arg
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Lys Trp Asn Leu Asp Ala
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Asn Asp Ser Leu Lys Thr
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Ser Ser Asn Leu Ser Arg
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Lys Ala Thr Arg Thr Thr
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Ser Ser Asn Arg Thr Lys
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Asn Ala Ser Arg Thr Arg
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Ser Ser Asp Leu Arg Arg
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Ser Asp Asn Leu Ser Glu
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Arg Ala Asn Arg Asn Ser
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Ser Asp Asn Leu Ala Arg
1               5

<210> SEQ ID NO 77
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Lys Val Asn Leu Met Ser
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Lys Val Asn Leu Arg Glu
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Ser Asp Thr Leu Ser Gln
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Lys Gln Thr Arg Thr Thr
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

His Arg Ser Ser Leu Arg Arg
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Ser Ala Asn Leu Ser Arg
```

```
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Trp His Ser Ser Leu Arg Val
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Ser Ala His Leu Ser Arg
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Ser Asp Val Leu Ser Val
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Asn Asn His Arg Ile Thr
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Pro Ser Ser Arg Arg Thr
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 88

Arg Ser Asp Ser Leu Ser Val
1            5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Asn Ala Asn Arg Lys Thr
1            5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Ser Asp Ser Leu Ser Thr
1            5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asp Arg Ala Asn Arg Ile Lys
1            5

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gctggtacac ggcagggtca ggg                                      23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
agagtctctc agctggtaca cgg                                      23

<210> SEQ ID NO 94
<211> LENGTH: 23
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 94
gagaatcaaa atcggtgaat agg                                              23

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
acaaaactgt gctagacatg agg                                              23

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
agagcaacag tgctgtggcc tgg                                              23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gacaccttct tccccagccc agg                                              23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ctcgaccagc ttgacatcac agg                                              23

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
aagttcctgt gatgtcaagc tgg                                              23

<210> SEQ ID NO 100
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 100
gtcgagaaaa gctttgaaac agg                                              23

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ttcggaaccc aatcactgac agg                                              23

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ccactttcag gaggaggatt cgg                                              23

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
acccggccac tttcaggagg agg                                              23

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gctggtacac ggcagggtca                                                  20

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gagagtctct cagctggtac a                                                21

<210> SEQ ID NO 106
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 106
gagaatcaaa atcggtgaat                                                     20

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gacaaaactg tgctagacat g                                                   21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gagagcaaca gtgctgtggc c                                                   21

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gacaccttct tccccagccc                                                     20

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gctcgaccag cttgacatca c                                                   21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gaagttcctg tgatgtcaag c                                                   21

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 112
gtcgagaaaa gctttgaaac                                          20

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gttcggaacc caatcactga c                                        21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gccactttca ggaggaggat t                                        21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gacccggcca ctttcaggag g                                        21

<210> SEQ ID NO 116
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
atatccagaa ccctgaccct gccgtgtacc agctgagaga ctctaaatcc agtgacaagt      60
ctgtctgcct attcaccgat tttgattctc aaacaaatgt gtcacaaagt aaggattctg     120
atgtgtatat cacagacaaa actgtgctag acatgaggtc tatggacttc aagagcaaca     180
gtgctgtggc ctggagcaac aaatctgact ttgcatgtgc aaacgccttc aacaacagca     240
ttattccaga agacaccttc ttccccagcc caggtaaggg cagctttggt gccttcgcag     300

<210> SEQ ID NO 117
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
tctggatgct gaaagaatgt ctgttttttcc ttttagaaag ttcctgtgat gtcaagctgg      60
tcgagaaaag ctttgaaaca ggtaagacag gggtctagcc                               100

<210> SEQ ID NO 118
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
aagcccataa ccgctgtggc ctcttggttt tacagatacg aacctaaact ttcaaaacct    60
gtcagtgatt gggttccgaa tcctcctcct gaaagtggcc gggtttaatc tgctcatgac   120
gctgcggctg tggtccagct gaggtgaggg gccttgaagc                         160

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Gln His Val Leu Gln Asn
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Ser Lys Thr Arg Thr Asn
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Thr Glu Asp Arg Leu Ala
1               5

<210> SEQ ID NO 122
<211> LENGTH: 9
<212> TYPE: PRT
<213> ORGANISM: Unknown
<220> FEATURE:
<223> OTHER INFORMATION: Description of Unknown:
      "LAGLIDADG" family motif peptide

<400> SEQUENCE: 122

Leu Ala Gly Leu Ile Asp Ala Asp Gly
1               5

<210> SEQ ID NO 123
<211> LENGTH: 28
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 123
tagcaattca ggaaatttga ctttccat                                              28

<210> SEQ ID NO 124
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tgtcggatgg atgaaaccca gacacata                                              28

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Arg Trp Tyr Leu Asp Lys
1               5
```

TARGETED DISRUPTION OF THE T CELL RECEPTOR

CROSS-REFERENCE TO RELATED APPLICATIONS

The present application claims the benefit of U.S. Provisional Application No. 62/269,365, filed Dec. 18, 2015 and U.S. Provisional No. 62/306,500, filed Mar. 10, 2016, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Apr. 6, 2017, is named 83250143SL.txt and is 27,582 bytes in size.

TECHNICAL FIELD

The present disclosure is in the field of genome modification of human cells, including lymphocytes and stem cells.

BACKGROUND

Gene therapy holds enormous potential for a new era of human therapeutics. These methodologies will allow treatment for conditions that have not been addressable by standard medical practice. Gene therapy can include the many variations of genome editing techniques such as disruption or correction of a gene locus, and insertion of an expressible transgene that can be controlled either by a specific exogenous promoter fused to the transgene, or by the endogenous promoter found at the site of insertion into the genome.

Delivery and insertion of the transgene are examples of hurdles that must be solved for any real implementation of this technology. For example, although a variety of gene delivery methods are potentially available for therapeutic use, all involve substantial tradeoffs between safety, durability and level of expression. Methods that provide the transgene as an episome (e.g. basic adenovirus (Ad), adeno-associated virus (AAV) and plasmid-based systems) are generally safe and can yield high initial expression levels, however, these methods lack robust episomal replication, which may limit the duration of expression in mitotically active tissues. In contrast, delivery methods that result in the random integration of the desired transgene (e.g. integrating lentivirus (LV)) provide more durable expression but, due to the untargeted nature of the random insertion, may provoke unregulated growth in the recipient cells, potentially leading to malignancy via activation of oncogenes in the vicinity of the randomly integrated transgene cassette. Moreover, although transgene integration avoids replication-driven loss, it does not prevent eventual silencing of the exogenous promoter fused to the transgene. Over time, such silencing results in reduced transgene expression for the majority of non-specific insertion events. In addition, integration of a transgene rarely occurs in every target cell, which can make it difficult to achieve a high enough expression level of the transgene of interest to achieve the desired therapeutic effect.

In recent years, a new strategy for transgene integration has been developed that uses cleavage with site-specific nucleases (e.g., zinc finger nucleases (ZFNs), transcription activator-like effector domain nucleases (TALENs), CRISPR/Cas system with an engineered crRNA/tracr RNA (single guide RNA') to guide specific cleavage, etc.) to bias insertion into a chosen genomic locus. See, e.g., U.S. Pat. Nos. 9,255,250; 9,045,763; 9,005,973; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983 and 20130177960 and 20150056705. Further, targeted nucleases are being developed based on the Argonaute system (e.g., from *T. thermophilus*, known as TtAgo', see Swarts et al (2014) *Nature* 507(7491): 258-261), which also may have the potential for uses in genome editing and gene therapy. This nuclease-mediated approach to transgene integration offers the prospect of improved transgene expression, increased safety and expressional durability, as compared to classic integration approaches, since it allows exact transgene positioning for a minimal risk of gene silencing or activation of nearby oncogenes.

The T cell receptor (TCR) is an essential part of the selective activation of T cells. Bearing some resemblance to an antibody, the antigen recognition part of the TCR is typically made from two chains, α and β, which co-assemble to form a heterodimer. The antibody resemblance lies in the manner in which a single gene encoding a TCR alpha and beta complex is put together. TCR alpha (TCR α) and beta (TCR β) chains are each composed of two regions, a C-terminal constant region and an N-terminal variable region. The genomic loci that encode the TCR alpha and beta chains resemble antibody encoding loci in that the TCR α gene comprises V and J segments, while the β chain locus comprises D segments in addition to V and J segments. For the TCR β locus, there are additionally two different constant regions that are selected from during the selection process. During T cell development, the various segments recombine such that each T cell comprises a unique TCR variable portion in the alpha and beta chains, called the complementarity determining region (CDR), and the body has a large repertoire of T cells which, due to their unique CDRs, are capable of interacting with unique antigens displayed by antigen presenting cells. Once a TCR α or β gene rearrangement has occurred, the expression of the second corresponding TCR α or TCR β is repressed such that each T cell only expresses one unique TCR structure in a process called 'antigen receptor allelic exclusion' (see Brady et al, (2010) *J Immunol* 185:3801-3808).

During T cell activation, the TCR interacts with antigens displayed as peptides on the major histocompatability complex (MHC) of an antigen presenting cell. Recognition of the antigen-MHC complex by the TCR leads to T cell stimulation, which in turn leads to differentiation of both T helper cells (CD4+) and cytotoxic T lymphocytes (CD8+) in memory and effector lymphocytes. These cells then can expand in a clonal manner to give an activated subpopulation within the whole T cell population capable of reacting to one particular antigen.

Adoptive cell therapy (ACT) is a developing form of cancer therapy based on delivering tumor-specific immune cells to a patient in order for the delivered cells to attack and clear the patient's cancer. ACT can involve the use of tumor-infiltrating lymphocytes (TILs) which are T-cells that are isolated from a patient's own tumor masses and expanded ex vivo to re-infuse back into the patient. This approach has been promising in treating metastatic melanoma, where in one study, a long term response rate of >50% was observed (see for example, Rosenberg et al (2011) *Clin Canc Res* 17(13): 4550). TILs are a promising source of cells because they are a mixed set of the patient's own cells that have T-cell receptors (TCRs) specific for the Tumor associated antigens (TAAs) present on the tumor (Wu et al (2012) *Cancer J* 18(2):160). Other approaches involve editing T cells isolated from a patient's blood such that they are engineered to be responsive to a tumor in some way (Kalos et al (2011) *Sci Transl Med* 3(95):95ra73).

Chimeric Antigen Receptors (CARs) are molecules designed to target immune cells to specific molecular targets expressed on cell surfaces. In their most basic form, they are receptors introduced into a cell that couple a specificity domain expressed on the outside of the cell to signaling pathways on the inside of the cell such that when the specificity domain interacts with its target, the cell becomes activated. Often CARs are made from emulating the functional domains of T-cell receptors (TCRs) where an antigen specific domain, such as a scFv or some type of receptor, is fused to the signaling domain, such as ITAMs and other co-stimulatory domains. These constructs are then introduced into a T-cell ex vivo allowing the T-cell to become activated in the presence of a cell expressing the target antigen, resulting in the attack on the targeted cell by the activated T-cell in a non-MHC dependent manner (see Chicaybam et al (2011) *Int Rev Immunol* 30:294-311) when the T-cell is re-introduced into the patient. Thus, adoptive cell therapy using T cells altered ex vivo with an engineered TCR or CAR is a very promising clinical approach for several types of diseases. For example, cancers and their antigens that are being targeted includes follicular lymphoma (CD20 or GD2), neuroblastoma (CD171), non-Hodgkin lymphoma (CD19 and CD20), lymphoma (CD19), glioblastoma (IL13Rα2), chronic lymphocytic leukemia or CLL and acute lymphocytic leukemia or ALL (both CD19). Virus specific CARs have also been developed to attack cells harboring virus such as HIV. For example, a clinical trial was initiated using a CAR specific for Gp100 for treatment of HIV (Chicaybam, ibid).

ACTRs (Antibody-coupled T-cell Receptors) are engineered T cell components that are capable of binding to an exogenously supplied antibody. The binding of the antibody to the ACTR component arms the T cell to interact with the antigen recognized by the antibody, and when that antigen is encountered, the ACTR comprising T cell is triggered to interact with antigen (see U.S. Patent Publication 20150139943).

One of the drawbacks of adoptive cell therapy however is the source of the cell product must be patient specific (autologous) to avoid potential rejection of the transplanted cells. This has led researchers to develop methods of editing a patient's own T cells to avoid this rejection. For example, a patient's T cells or hematopoietic stem cells can be manipulated ex vivo with the addition of an engineered CAR, ACTR and/or T cell receptor (TCR), and then further treated with engineered nucleases to knock out T cell check point inhibitors such as PD1 and/or CTLA4 (see PCT publication WO2014/059173). For application of this technology to a larger patient population, it would be advantageous to develop a universal population of cells (allogeneic). In addition, knockout of the TCR will result in cells that are unable to mount a graft-versus-host disease (GVHD) response once introduced into a patient.

Thus, there remains a need for methods and compositions that can be used to modify (e.g., knock out) TCR expression in T cells.

SUMMARY

Disclosed herein are compositions and methods for partial or complete inactivation or disruption of a TCR gene and compositions and methods for introducing and expressing to desired levels of exogenous TCR transgenes in T lymphocytes, after or simultaneously with the disruption of the endogenous TCR. Additionally, provided herein are methods and compositions for deleting (inactivating) or repressing a TCR gene to produce TCR null T cell, stem cell, tissue or whole organism, for example a cell that does not express one or more T cell receptors on its surface. In certain embodiments, the TCR null cells or tissues are human cells or tissues that are advantageous for use in transplants. In preferred embodiments, the TCR null T cells are prepared for use in adoptive T cell therapy.

In one aspect, described herein is an isolated cell (e.g., a eukaryotic cell such as a mammalian cell including a lymphoid cell, a stem cell (e.g., iPSC, embryonic stem cell, MSC or HSC), or a progenitor cell) in which expression of a TCR gene is modulated by modification of exon c1, c2 and/or c3 of the TCR gene. In certain embodiments, the modification is to a sequence as shown in one or more of SEQ ID NO: 8-21 and/or 92-103; within 1-5, within 1-10 or within 1-20 base pairs on either side (the flanking genomic sequence) of SEQ ID NO:8-21 and/or 92-103; or within AACAGT, AGTGCT, CTCCT, TTGAAA, TGGACTT and AATCCTC. The modification may be by an exogenous fusion molecule comprising a functional domain (e.g., transcriptional regulatory domain, nuclease domain) and a DNA-binding domain, including, but not limited to: (i) a cell comprising an exogenous transcription factor comprising a DNA-binding domain that binds to a target site as shown in any of SEQ ID NO:8-21 and/or 92-103 and a transcriptional regulatory domain in which the transcription factor modifies B2M gene expression and/or (ii) a cell comprising an insertion and/or a deletion within one or more of SEQ ID NO:8-21 and/or 92-103; within 1-5, within 1-10 or within 1-20 base pairs on either side (the flanking genomic sequence) of SEQ ID NO: 8-21 and/or 92-103; or within AACAGT, AGTGCT, CTCCT, TTGAAA, TGGACTT and AATCCTC. The cell may include further modifications, for example an inactivated T-cell receptor gene, PD1 and/or CTLA4 gene and/or a transgene a transgene encoding a chimeric antigen receptor (CAR), a transgene encoding an Antibody-coupled T-cell Receptor (ACTR) and/or a transgene encoding an antibody. Pharmaceutical compositions comprising any cell as described herein are also provided as well as methods of using the cells and pharmaceutical compositions in ex vivo therapies for the treatment of a disorder (e.g., a cancer) in a subject.

Thus, in one aspect, described herein are cells in which the expression of a TCR gene is modulated (e.g., activated, repressed or inactivated). In preferred embodiments, exon c1, c2 and/or c3 of a TCR gene is modulated. The modulation may be by an exogenous molecule (e.g., engineered transcription factor comprising a DNA-binding domain and a transcriptional activation or repression domain) that binds to the TCR gene and regulates TCR expression and/or via sequence modification of the TCR gene (e.g., using a nuclease that cleaves the TCR gene and modifies the gene sequence by insertions and/or deletions). In some embodiments, cells are described that comprise an engineered nuclease to cause a knockout of a TCR gene. In other embodiments, cells are described that comprise an engineered transcription factor (TF) such that the expression of a TCR gene is modulated. In some embodiments, the cells are T cells. Further described are cells wherein the expression of a TCR gene is modulated and wherein the cells are further engineered to comprise a least one exogenous transgene and/or an additional knock out of at least one endogenous gene (e.g., beta 2 microglobuin (B2M) and/or immunological checkpoint gene such as PD1 and/or CTLA4) or combinations thereof. The exogenous transgene may be integrated into a TCR gene (e.g., when the TCR gene is knocked out) and/or may be integrated into a non-TCR gene such as a safe harbor gene. In some cases, the exogenous transgene encodes an ACTR and/or a CAR. The transgene construct may be inserted by either HDR- or NHEJ-driven processes. In some aspects the cells with modulated TCR expression comprise at least an exogenous ACTR and an exogenous CAR. Some cells comprising a TCR modulator further comprise a knockout of one or more check point inhibitor genes. In some embodiments, the check point inhibitor is PD1. In other embodiments, the check point inhibitor is CTLA4. In further aspects, the TCR modulated cell comprises a PD1 knockout and a CTLA4 knockout. In some embodiments, the TCR gene modulated is a gene encoding TCR β (TCRB). In some embodiments this is achieved via targeted cleavage of the constant region of this gene (TCR β Constant region, or TRBC). In certain embodiments, the TCR gene modulated is a gene encoding TCR α (TCRA). In further embodiments, insertion is achieved via targeted cleavage of the constant region of a TCR gene, including targeted cleavage of the constant region of a TCR α gene (referred to herein as "TRAC" sequences). In some embodiments, the TCR gene modified cells are further modified at the B2M gene, the HLA-A, -B, -C genes, or the TAP gene, or any combination thereof. In other embodiments, the regulator for HLA class II, CTLA, is also modified.

In certain embodiments, the cells described herein comprise a modification (e.g., deletion and/or insertion, binding of an engineered TF to repress TCR expression) to a TCRA gene (e.g., modification of exon c1, exon c2 and/or exon c3). In certain embodiments, the modification is of SEQ ID NO:8-21 and/or 92-103, including modification by binding to, cleaving, inserting and/or deleting one or more nucleotides within any of these sequences and/or within 1-50 base pairs (including any value therebetween such as 1-5, 1-10 or 1-20 base pairs) of the gene (genomic) sequences flanking these sequences in the TCRA gene. In certain embodiments, the cells comprise a modification (binding to, cleaving, insertions and/or deletions) within one or more of the following sequences: AACAGT, AGTGCT, CTCCT, TTGAAA, TGGACTT and AATCCTC within a TCRA gene (e.g., exon c1, c2 and/or c3, see FIG. 1B). In certain embodiments, the modification comprises binding of an engineered TF as described herein such that a TCRA gene expression is modulated, for example, repressed or activated. In other embodiments, the modification is a genetic modification (alteration of nucleotide sequence) at or near nuclease(s) binding (target) and/or cleavage site(s), including but not limited to, modifications to sequences within 1-300 (or any number of base pairs therebetween) base pairs upstream, downstream and/or including 1 or more base pairs of the site(s) of cleavage and/or binding site; modifications within 1-100 base pairs (or any number of base pairs therebetween) of including and/or on either side of the binding and/or cleavage site(s); modifications within 1 to 50 base pairs (or any number of base pairs therebetween) including and/or on either side (e.g., 1 to 5, 1 to 10, 1 to 20 or more base pairs) of the binding and/or cleavage site(s); and/or modifications to one or more base pairs within the nuclease binding site and/or cleavage site. In certain embodiments, the modification is at or near (e.g., 1-300 base pairs, 1-50, 1-20, 1-10 or 1-5 or any number of base pairs therebetween) of the TCRA gene sequence surrounding any of SEQ ID NOs:8-21 or 92-103. In certain embodiments, the modification includes modifications of a TCRA gene within one or more of the sequences shown in SEQ ID NOs:6 to 48 or 137 through 205 or within AACAGT, AGTGCT, CTCCT, TTGAAA, TGGACTT and AATCCTC of a TCR gene (e.g., exon c1, c2 and/or c3), for example a modification of 1 or more base pairs to one or more of these sequences. In certain embodiments, the nuclease-mediated genetic modifications are between paired target sites (when a dimer is used to cleave the target). The nuclease-mediated genetic modifications may include insertions and/or deletions of any number of base pairs, including insertions of non-coding sequences of any length and/or transgenes of any length and/or deletions of 1 base pair to over 1000 kb (or any value therebetween including, but not limited to, 1-100 base pairs, 1-50 base pairs, 1-30 base pairs, 1-20 base pairs, 1-10 base pairs or 1-5 base pairs).

The modified cells of the invention may be a eukaryotic cell, including a non-human mammalian and a human cell such as lymphoid cell (e.g., a T-cell), a stem/progenitor cell (e.g., an induced pluripotent stem cell (iPSC), an embryonic stem cell (e.g., human ES), a mesenchymal stem cell (MSC), or a hematopoietic stem cell (HSC). The stem cells may be totipotent or pluripotent (e.g., partially differentiated such as an HSC that is a pluripotent myeloid or lymphoid stem cell). In other embodiments, the invention provides methods for producing cells that have a null genotype for TCR expression. Any of the modified stem cells described herein (modified at the TCRA locus) may then be differentiated to generate a differentiated (in vivo or in vitro) cell descended from a stem cell as described herein with modified TCRA gene expression.

In another aspect, the compositions (modified cells) and methods described herein can be used, for example, in the treatment or prevention or amelioration of a disorder. The methods typically comprise (a) cleaving or down regulating an endogenous TCR gene in an isolated cell (e.g., T-cell or lymphocyte) using a nuclease (e.g., ZFN or TALEN) or nuclease system such as CRISPR/Cas with an engineered crRNA/tracr RNA, or using an engineered transcription factor (e.g. ZFN-TF, TALE-TF, Cfp1-TF or Cas9-TF) such that the TCR gene is inactivated or down modulated; and (b) introducing the cell into the subject, thereby treating or preventing the disorder. In some embodiments, the gene encoding TCR β (TCRB) is inactivated or down modulated. In some embodiments inactivation is achieved via targeted cleavage of the constant region of this gene (TCR β Constant region, or TRBC). In preferred embodiments, the gene encoding TCR α (TCRA) is inactivated or down modulated. In further preferred embodiments, the disorder is a cancer or an infectious disease. In further preferred embodiments inactivation is achieved via targeted cleavage of the constant region of this gene (TCR α Constant region, or abbreviated as TRAC). In some embodiments, the additional genes are modulated (knocked-out), for example, B2M, PD1 and/or CTLA4 and/or one or more therapeutic transgenes are present in the cell (episomal, randomly integrated or integrated via targeted integration such as nuclease-mediated integration).

The transcription factor(s) and/or nuclease(s) can be introduced into a cell or the surrounding culture media as mRNA, in protein form and/or as a DNA sequence encoding the nuclease(s). In certain embodiments, the isolated cell introduced to the subject further comprises additional genomic modification, for example, an integrated exogenous sequence (into the cleaved TCR gene or a different gene, for example a safe harbor gene or locus) and/or inactivation (e.g., nuclease-mediated) of additional genes, for example one or more HLA genes. The exogenous sequence or protein may be introduced via a vector (e.g. Ad, AAV, LV), or by using a technique such as electroporation. In some embodiments, the proteins are introduced into the cell by cell squeezing (see Kollmannsperger et al (2016) *Nat Comm* 7, 10372 doi:10.1038/ncomms10372). In some aspects, the composition may comprise isolated cell fragments and/or differentiated (partially or fully) cells.

In some aspects, the mature cells may be used for cell therapy, for example, for adoptive cell transfer. In other embodiments, the cells for use in T cell transplant contain another gene modification of interest. In one aspect, the T cells contain an inserted chimeric antigen receptor (CAR) specific for a cancer marker. In a further aspect, the inserted CAR is specific for the CD19 marker characteristic of B cells, including B cell malignancies. Such cells would be useful in a therapeutic composition for treating patients without having to match HLA, and so would be able to be used as an "off-the-shelf" therapeutic for any patient in need thereof.

In another aspect, the TCR-modulated (modified) T cells contain an inserted Antibody-coupled T-cell Receptor (ACTR) donor sequence. In some embodiments, the ACTR donor sequence is inserted into a TCR gene to disrupt expression of that TCR gene following nuclease induced cleavage. In other embodiments, the donor sequence is inserted into a "safe harbor" locus, such as the AAVS1, HPRT, albumin and CCR5 genes. In some embodiments, the ACTR sequence is inserted via targeted integration where the ACTR donor sequence comprises flanking homology arms that have homology to the sequence flanking the cleavage site of the engineered nuclease. In some embodiments the ACTR donor sequence further comprises a promoter and/or other transcriptional regulatory sequences. In other embodiments, the ACTR donor sequence lacks a promoter. In some embodiments, the ACTR donor is inserted into a TCR β encoding gene (TCRB). In some embodiments insertion is achieved via targeted cleavage of the constant region of this gene (TCR β Constant region, or TRBC). In preferred embodiments, the ACTR donor is inserted into a TCR α encoding gene (TCRA). In further preferred embodiments insertion is achieved via targeted cleavage of the constant region of this gene (TCR α Constant region, abbreviated TRAC). In some embodiments, the donor is inserted into an exon sequence in TCRA, while in others, the donor is inserted into an intronic sequence in TCRA. In some embodiments, the TCR-modulated cells further comprise a CAR. In still further embodiments, the TCR-modulated cells are additionally modulated at an HLA gene or a checkpoint inhibitor gene.

Also provided are pharmaceutical compositions comprising the modified cells as described herein (e.g., T cells or stem cells with inactivated TCR gene), or pharmaceutical compositions comprising one or more of the TCR gene binding molecules (e.g., engineered transcription factors and/or nucleases) as described herein. In certain embodiments, the pharmaceutical compositions further comprise one or more pharmaceutically acceptable excipients. The modified cells, TCR gene binding molecules (or polynucleotides encoding these molecules) and/or pharmaceutical compositions comprising these cells or molecules are introduced into the subject via methods known in the art, e.g. through intravenous infusion, infusion into a specific vessel such as the hepatic artery, or through direct tissue injection (e.g. muscle). In some embodiments, the subject is an adult human with a disease or condition that can be treated or ameliorated with the composition. In other embodiments, the subject is a pediatric subject where the composition is administered to prevent, treat or ameliorate the disease or condition (e.g., cancer, graft versus host disease, etc.).

In some aspects, the composition (TCR modulated cells comprising an ACTR) further comprises an exogenous antibody. See, also, U.S. Publication No. 20170196992. In some aspects, the antibody is useful for arming an ACTR-comprising T cell to prevent or treat a condition. In some embodiments, the antibody recognizes an antigen associated with a tumor cell or with cancer associate processes such as EpCAM, CEA, gpA33, mucins, TAG-72, CAIX, PSMA, folate-binding antibodies, CD19, EGFR, ERBB2, ERBB3, MET, IGF1R, EPHA3, TRAILR1, TRAILR2, RANKL, FAP, VEGF, VEGFR, αVβ3 and α5β1 integrins, CD20, CD30, CD33, CD52, CTLA4, and enascin (Scott et al (2012) *Nat Rev Cancer* 12:278). In other embodiments, the antibody recognizes an antigen associated with an infectious disease such as HIV, HCV and the like.

In another aspect, provided herein are TCR gene DNA-binding domains (e.g., ZFPs, TALEs and sgRNAs) that bind to a target site in a TCR gene. In certain embodiments, the DNA binding domain comprises a ZFP with the recognition helix regions in the order as shown in a single row of Table 1; a TAL-effector domain DNA-binding protein with the RVDs that bind to a target site as shown in the first column of Table 1 or the third column of Table 2; and/or a sgRNA as shown in a single row of Table 2. These DNA-binding proteins can be associated with transcriptional regulatory domains to form engineered transcription factors that modulate TCR expression. Alternatively, these DNA-binding proteins can be associated with one or more nuclease domains to form engineered zinc finger nucleases (ZFNs), TALENs and/or CRISPR/Cas systems that bind to and cleave a TCR gene. In certain embodiments, the ZFNs, TALENs or single guide RNAs (sgRNA) of a CRISPR/Cas system bind to target sites in a human TCR gene. The DNA-binding domain of the transcription factor or nuclease (e.g., ZFP, TALE, sgRNA) may bind to a target site in a TCRA gene comprising 9, 10, 11 12 or more (e.g., 13, 14, 15, 16, 17, 18, 19, 20 or more) nucleotides of any of SEQ ID NOs:8-21 and/or 92-103. The zinc finger proteins may include 1, 2, 3, 4, 5, 6 or more zinc fingers, each zinc finger having a recognition helix that specifically contacts a target subsite in the target gene. In certain embodiments, the zinc finger proteins comprise 4 or 5 or 6 fingers (designated F1, F2, F3, F4, F5 and F6 and ordered F1 to F4 or F5 or F6 from N-terminus to C-terminus), for example as shown in Table 1. In other embodiments, the single guide RNAs or TAL-effector DNA-binding domains may bind to a target site shown in any of SEQ ID NOs: 8-21 and/or 92-103 (or 12 or more base pairs within any of SEQ ID Nos: 8-21 and/or 92-103). Exemplary sgRNA target sites are shown in SEQ ID NO:92-103. TALENs may be designed to target sites as described herein using canonical or non-canonical RVDs as described in U.S. Pat. Nos. 8,586,526 and 9,458,205. The nucleases described herein (comprising a ZFP, a TALE or a sgRNA DNA-binding domain) are capable of making genetic modifications within a TCRA gene comprising any of SEQ ID NO:8-21 and/or 92-103, including modifications (insertions and/or deletions) within any of these sequences (SEQ ID NO:8-21 and/or 92-103) and/or modifications to TCRA gene sequences flanking the target site sequences shown in SEQ ID NO:8-21 and/or 92-103, for instance modifications within exon c1, c2 and/or c3 of a TCR gene within one or more of the following sequences: AACAGT, AGTGCT, CTCCT, TTGAAA, TGGACTT and AATCCTC.

Any of the proteins described herein may further comprise a cleavage domain and/or a cleavage half-domain (e.g., a wild-type or engineered FokI cleavage half-domain). Thus, in any of the nucleases (e.g., ZFNs, TALENs, CRISPR/Cas systems) described herein, the nuclease domain may comprise a wild-type nuclease domain or nuclease half-domain (e.g., a FokI cleavage half domain). In other embodiments, the nucleases (e.g., ZFNs, TALENs, CRISPR/Cas nucleases) comprise engineered nuclease domains or half-domains, for example engineered FokI cleavage half domains that form obligate heterodimers. See, e.g., U.S. Pat. Nos. 7,914,796 and 8,034,598.

In another aspect, the disclosure provides a polynucleotide encoding any of the proteins, fusion molecules and/or components thereof (e.g., sgRNA or other DNA-binding domain) described herein. The polynucleotide may be part of a viral vector, a non-viral vector (e.g., plasmid) or be in mRNA form. Any of the polynucleotides described herein may also comprise sequences (donor, homology arms or patch sequences) for targeted insertion into the TCR α and/or the TCR β gene. In yet another aspect, a gene delivery vector comprising any of the polynucleotides described herein is provided. In certain embodiments, the vector is an adenoviral vector (e.g., an Ad5/F35 vector) or a lentiviral vector (LV) including integration competent or integration-defective lentiviral vectors or an adeno-associated vector (AAV). Thus, also provided herein are viral vectors comprising a sequence encoding a nuclease (e.g. ZFN or TALEN) and/or a nuclease system (CRISPR/Cas or Ttago) and/or a donor sequence for targeted integration into a target gene. In some embodiments, the donor sequence and the sequences encoding the nuclease are on different vectors. In other embodiments, the nucleases are supplied as polypeptides. In preferred embodiments, the polynucleotides are mRNAs. In some aspects, the mRNA may be chemically modified (See e.g. Kormann et al, (2011) *Nature Biotechnology* 29(2):154-157). In other aspects, the mRNA may comprise an ARCA cap (see U.S. Pat. Nos. 7,074,596 and 8,153,773). In some aspects, the mRNA may comprise a cap introduced by enzymatic modification. The enzymatically introduced cap may comprise Cap0, Cap1 or Cap2 (see e.g. Smietanski et al, (2014) *Nature Communications* 5:3004). In further aspects, the mRNA may be capped by chemical modification. In further embodiments, the mRNA may comprise a mixture of unmodified and modified nucleotides (see U.S. Patent Publication 2012-0195936). In still further embodiments, the mRNA may comprise a WPRE element (see U.S. Patent Publication No. 20160326548). In some embodiments, the mRNA is double stranded (See e.g. Kariko et al (2011) *Nucl Acid Res* 39:e142).

In yet another aspect, the disclosure provides an isolated cell comprising any of the proteins, polynucleotides and/or vectors described herein. In certain embodiments, the cell is selected from the group consisting of a stem/progenitor cell, or a T-cell (e.g., CD4$^+$ T-cell). In a still further aspect, the disclosure provides a cell or cell line which is descended from a cell or line comprising any of the proteins, polynucleotides and/or vectors described herein, namely a cell or cell line descended (e.g., in culture) from a cell in which TCR has been inactivated by one or more ZFNs and/or in which a donor polynucleotide (e.g. ACTR and/or CAR) has been stably integrated into the genome of the cell. Thus, descendants of cells as described herein may not themselves comprise the proteins, polynucleotides and/or vectors described herein, but, in these cells, a TCR gene is inactivated and/or a donor polynucleotide is integrated into the genome and/or expressed.

In another aspect, described herein are methods of inactivating a TCR gene in a cell by introducing one or more proteins, polynucleotides and/or vectors into the cell as described herein. In any of the methods described herein the nucleases may induce targeted mutagenesis, deletions of cellular DNA sequences, and/or facilitate targeted recombination at a predetermined chromosomal locus. Thus, in certain embodiments, the nucleases delete and/or insert one or more nucleotides from or into the target gene. In some embodiments the TCR gene is inactivated by nuclease cleavage followed by non-homologous end joining. In other embodiments, a genomic sequence in the target gene is replaced, for example using a nuclease (or vector encoding said nuclease) as described herein and a "donor" sequence that is inserted into the gene following targeted cleavage with the nuclease. The donor sequence may be present in the nuclease vector, present in a separate vector (e.g., AAV, Ad or LV vector) or, alternatively, may be introduced into the cell using a different nucleic acid delivery mechanism.

Furthermore, any of the methods described herein can be practiced in vitro, in vivo and/or ex vivo. In certain embodiments, the methods are practiced ex vivo, for example to modify T-cells, to make them useful as therapeutics in an allogenic setting to treat a subject (e.g., a subject with cancer). Non-limiting examples of cancers that can be treated and/or prevented include lung carcinomas, pancreatic cancers, liver cancers, bone cancers, breast cancers, colorectal cancers, leukemias, ovarian cancers, lymphomas, brain cancers and the like.

BRIEF DESCRIPTION OF THE DRAWINGS

FIGS. 1A and 1B are a depiction of the TCRA gene showing the locations of the sites targeted by the nucleases. FIG. 1A is an illustration of the processing of the TCRA gene from the germline form to that of a mature T cell and indicates the general target of the nucleases. FIG. 1B (SEQ ID NOs:116 (exon c1), 117 (exon c2) and 118 (exon c3)) shows the regions between the target sites in the constant region sequence. The sequence shown in uppercase black lettering is the sequence of the indicated exon sequence, while the sequence in lowercase grey lettering is the adjoining intron sequence.

FIGS. 5A through 5D are graphs depicting the growth of T cells following treatment with the TCRA-specific ZFN grouped according to the target site in the TCRA gene.

FIG. 6 shows results from TRAC (TCRA) and B2M double knockout and targeted integration of a donor into either the TRAC (TCRA) or B2M locus.

DETAILED DESCRIPTION

Figure 2A:
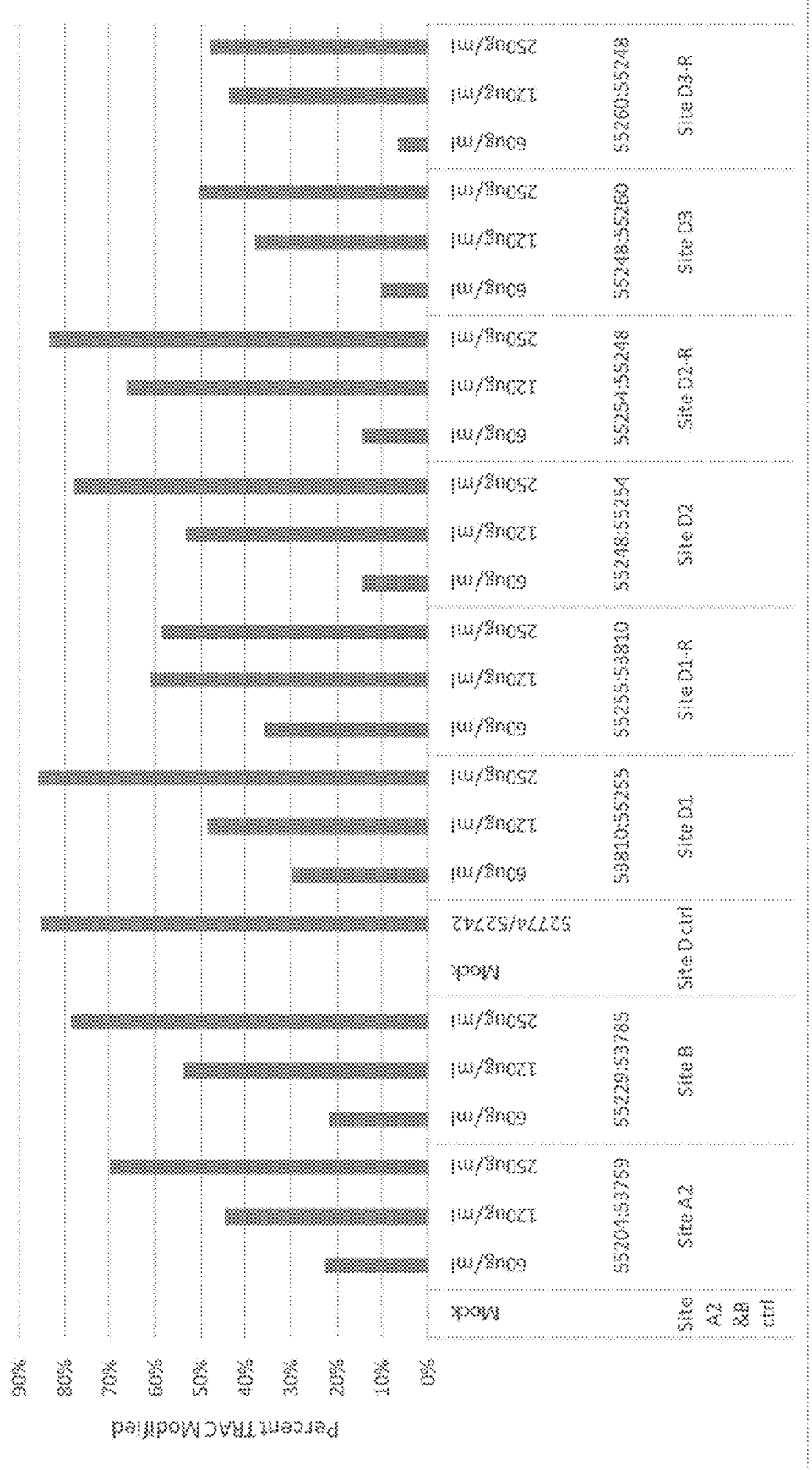
FIGS. 2A and 2B are graphs depicting the percent of each site modified in T cells treated with ZFNs specific for TCRA sites A, B and D (FIG. 2A) and sites E, F and G (FIG. 2B). Many of the pairs gave modification rates of 80% or greater.

Disclosed herein are compositions and methods for generating cells in which expression of a TCR gene is modulated such that the cells no longer comprise a TCR on their cell surfaces. Cells modified in this manner can be used as therapeutics, for example, transplants, as the lack of a TCR complex prevents or reduces an HLA-based immune response. Additionally, other genes of interest may be inserted into cells in which the TCR gene have been manipulated and/or other genes of interest may be knocked out.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$. "Non-specific binding" refers to, non-covalent interactions that occur between any molecule of interest (e.g. an engineered nuclease) and a macromolecule (e.g. DNA) that are not dependent on target sequence.

A "DNA binding molecule" is a molecule that can bind to DNA. Such DNA binding molecule can be a polypeptide, a domain of a protein, a domain within a larger protein or a polynucleotide. In some embodiments, the polynucleotide is DNA, while in other embodiments, the polynucleotide is RNA. In some embodiments, the DNA binding molecule is a protein domain of a nuclease (e.g. the FokI domain), while in other embodiments, the DNA binding molecule is a guide RNA component of an RNA-guided nuclease (e.g. Cas9 or Cfp1).

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains, each comprising a repeat variable diresidue (RVD), are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. TALE proteins may be designed to bind to a target site using canonical or non-canonical RVDs within the repeat units. See, e.g., U.S. Pat. Nos. 8,586,526 and 9,458, 205. Zinc finger and TALE DNA-binding domains can be "engineered" to bind to a predetermined nucleotide sequence, for example via engineering (altering one or more amino acids) of the recognition helix region of a naturally occurring zinc finger protein or by engineering of the amino acids involved in DNA binding (the repeat variable diresidue or RVD region). Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs (canonical and non-canonical RVDs) and binding data. See, for example, U.S. Pat. Nos. 9,458,205; 8,586,526; 6,140,081; 6,453,242; and 6,534,261; see also WO 98/53058; WO 98/53059; WO 98/53060; WO 02/016536 and WO 03/016496.

A "selected" zinc finger protein, TALE protein or CRISPR/Cas system is not found in nature and whose production results primarily from an empirical process such as phage display, interaction trap or hybrid selection. See e.g., U.S. Pat. Nos. 5,789,538; 5,925,523; 6,007,988; 6,013, 453; 6,200,759; WO 95/19431; WO 96/06166; WO 98/53057; WO 98/54311; WO 00/27878; WO 01/60970; WO 01/88197 and WO 02/099084.

"TtAgo" is a prokaryotic Argonaute protein thought to be involved in gene silencing. TtAgo is derived from the bacteria *Thermus thermophilus*. See, e.g. Swarts et al, ibid, G. Sheng et al., (2013) *Proc. Natl. Acad. Sci. U.S.A.* 111, 652). A "TtAgo system" is all the components required including e.g. guide DNAs for cleavage by a TtAgo enzyme.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break (DSB) in the target sequence (e.g., cellular chromatin) at a predetermined site (e.g. a gene or locus of interest), and a "donor" polynucleotide, having homology to the nucleotide sequence in the region of the break, can be introduced into the cell. The presence of the DSB has been shown to facilitate integration of the donor sequence. Optionally, the construct has homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,888,121; 7,914,796; 8,034,598; 8,623,618 and U.S. Patent Publication No. 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5' GAATTC 3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. See, e.g., U.S. Pat. Nos. 8,703,489 and 9,255,259. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid. The term also includes systems in which a polynucleotide component associates with a polypeptide component to form a functional molecule (e.g., a CRISPR/Cas system in which a single guide RNA associates with a functional domain to modulate gene expression).

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples of safe harbor loci that are targeted by nuclease(s) include CCR5, CCR5, HPRT, AAVS1, Rosa and albumin. See, e.g., U.S. Pat. Nos. 8,771, 985; 8,110,379; 7,951,925; U.S. Publication Nos. 20100218264; 20110265198; 20130137104; 20130122591; 20130177983; 20130177960; 20150056705 and 20150159172).

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. "Modulation" or "modification" of gene expression refers to a change in the activity of a gene. Modulation of expression can include, but is not limited to, gene activation and gene repression, including by modification of the gene via binding of an exogenous molecule (e.g., engineered transcription factor). Modulation may also be achieved by modification of the gene sequence via genome editing (e.g., cleavage, alteration, inactivation, random mutation). Gene inactivation refers to any reduction in gene expression as compared to a cell that has not been modified as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a DNA-binding domain (e.g., ZFP, TALE) is fused to an activation domain, the DNA-binding domain and the activation domain are in operative linkage if, in the fusion polypeptide, the DNA-binding domain portion is able to bind its target site and/or its binding site, while the activation domain is able to up-regulate gene expression. When a fusion polypeptide in which a DNA-binding domain is fused to a cleavage domain, the DNA-binding domain and the cleavage domain are in operative linkage if, in the fusion polypeptide, the DNA-binding domain portion is able to bind its target site and/or its binding site, while the cleavage domain is able to cleave DNA in the vicinity of the target site. Similarly, with respect to a fusion polypeptide in which a DNA-binding domain is fused to an activation or repression domain, the DNA-binding domain and the activation or repression domain are in operative linkage if, in the fusion polypeptide, the DNA-binding domain portion is able to bind its target site and/or its binding site, while the activation domain is able to upregulate gene expression or the repression domain is able to downregulate gene expression.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the expression cassettes of the invention can be administered. Subjects of the present invention include those with a disorder or those at risk for developing a disorder.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Cancer and graft versus host disease are non-limiting examples of conditions that may be treated using the compositions and methods described herein. Thus, "treating" and "treatment" includes:

(i) preventing the disease or condition from occurring in a mammal, in particular, when such mammal is predisposed to the condition but has not yet been diagnosed as having it;
(ii) inhibiting the disease or condition, i.e., arresting its development;
(iii) relieving the disease or condition, i.e., causing regression of the disease or condition; or
(iv) relieving the symptoms resulting from the disease or condition, i.e., relieving pain without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a mammal, preferably a human, is sufficient to effect treatment in the mammal, preferably a human. The amount of a composition of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

DNA-binding Domains

Described herein are compositions comprising a DNA-binding domain that specifically binds to a target site in any gene comprising a HLA gene or a HLA regulator. Any DNA-binding domain can be used in the compositions and methods disclosed herein, including but not limited to a zinc finger DNA-binding domain, a TALE DNA binding domain, the DNA-binding portion (sgRNA) of a CRISPR/Cas nuclease, or a DNA-binding domain from a meganuclease. The DNA-binding domain may bind to any target sequence within the gene, including, but not limited to, a target sequence of 12 or more nucleotides as shown in any of target sites disclosed herein (SEQ ID NO:8-21 and/or 92-103).

In certain embodiments, the DNA binding domain comprises a zinc finger protein. Preferably, the zinc finger protein is non-naturally occurring in that it is engineered to bind to a target site of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties. In certain embodiments, the DNA-binding domain comprises a zinc finger protein disclosed in U.S. Patent Publication No. 2012/0060230 (e.g., Table 1), incorporated by reference in its entirety herein.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in U.S. Pat. No. 6,794,136.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA binding domain is an engineered zinc finger protein that binds (in a sequence-specific manner) to a target site in a TCR gene or TCR regulatory gene and modulates expression of a TCR gene. In some embodiments, the zinc finger protein binds to a target site in TCRA, while in other embodiments, the zinc finger binds to a target site in TRBC.

Usually, the ZFPs include at least three fingers. Certain of the ZFPs include four, five or six fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains.

In some embodiments, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

In other embodiments, the DNA binding domain comprises an engineered domain from a TAL effector similar to those derived from the plant pathogens *Xanthomonas* (see Boch et al, (2009) *Science* 326: 1509-1512 and Moscou and Bogdanove, (2009) *Science* 326: 1501) and Ralstonia (see Heuer et al (2007) *Applied and Environmental Microbiology* 73(13): 4379-4384); U.S. Patent Publication Nos. 20110301073 and 20110145940. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et al (2007) Science_318:648-651). These proteins contain a DNA binding domain and a transcriptional activation domain. One of the most well characterized TALEs is AvrBs3 from *Xanthomonas campestgris* pv. *Vesicatoria* (see Bonas et al (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Specificity of these TAL effectors depends on the sequences found in the tandem repeats. The repeated sequence comprises approximately 102 base pairs and the repeats are typically 91-100% homologous with each other (Bonas et al, ibid). Polymorphism of the repeats is usually located at positions 12 and 13 and there appears to be a one-to-one correspondence between the identity of the hypervariable diresidues (the repeat variable diresidue or RVD region) at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 (Repeat Variable Diresidue or RVD) leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN), including TAL-ENs with atypical RVDs. See, e.g., U.S. Pat. No. 8,586,526.

In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) *Nucl Acid Res:* 1-13, doi: 10.1093/nar/gkt1224).

In still further embodiments, the nuclease comprises a compact TALEN. These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al (2013) *Nat Comm:* 1-8 DOI: 10.1038/ncomms2782). In addition, the nuclease domain may also exhibit DNA-binding functionality. Any TALENs may be used in combination with additional TALENs (e.g., one or more TALENs (cTALENs or FokI-TALENs) with one or more mega-TALEs.

In addition, as disclosed in these and other references, zinc finger domains and/or multi-fingered zinc finger proteins or TALEs may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in U.S. Pat. No. 6,794,136.

In certain embodiments, the DNA-binding domain is part of a CRISPR/Cas nuclease system, including a single guide RNA (sgRNA) that binds to DNA. See, e.g., U.S. Pat. No. 8,697,359 and U.S. Patent Publication Nos. 20150056705 and 20150159172. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1:7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs functional domain (e.g., nuclease such as Cas) to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof such as derivative Cas proteins. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. In some embodiments, the Cas protein is a small Cas9 ortholog for delivery via an AAV vector (Ran et al (2015) *Nature* 520, p. 186).

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G.

Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37° C. Ago-RNA-mediated DNA cleavage could be used to affect a panopoly of outcomes including gene knock-out, targeted gene addition, gene correction, targeted gene deletion using techniques standard in the art for exploitation of DNA breaks.

Thus, any DNA-binding domain can be used.

Fusion Molecules

Fusion molecules comprising DNA-binding domains (e.g., ZFPs or TALEs, CRISPR/Cas components such as single guide RNAs) as described herein associated with a heterologous regulatory (functional) domain (or functional fragment thereof) are also provided. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. Such fusion molecules include transcription factors comprising the DNA-binding domains described herein and a transcriptional regulatory domain as well as nucleases comprising the DNA-binding domains and one or more nuclease domains.

Suitable domains for achieving activation (transcriptional activation domains) include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Barik, *J. Virol.* 72:5610-5618 (1998) and Doyle & Hunt, *Neuroreport* 8:2937-2942 (1997)); Liu et al., *Cancer Gene Ther.* 5:3-28 (1998)), or artificial chimeric functional domains such as VP64 (Beerli et al., (1998) *Proc. Natl. Acad. Sci. USA* 95:14623-33), and degron (Molinari et al., (1999) *EMBO J.* 18, 6439-6447). Additional exemplary activation domains include, Oct 1, Oct-2A, Sp1, AP-2, and CTF1 (Seipel et al., *EMBO J.* 11, 4961-4968 (1992) as well as p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5,-6,-7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

It will be clear to those of skill in the art that, in the formation of a fusion protein (or a nucleic acid encoding same) between a DNA-binding domain and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in U.S. Pat. No. 7,053,264.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

Fusion molecules are constructed by methods of cloning and biochemical conjugation that are well known to those of skill in the art. Fusion molecules comprise a DNA-binding domain (e.g., ZFP, TALE, sgRNA) associated with a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) *Proc. Natl. Acad. Sci. USA* 97:3930-3935. Furthermore, single guide RNAs of the CRISPR/Cas system associate with functional domains to form active transcriptional regulators and nucleases.

In certain embodiments, the target site is present in an accessible region of cellular chromatin. Accessible regions can be determined as described, for example, in U.S. Pat. Nos. 7,217,509 and 7,923,542. If the target site is not present in an accessible region of cellular chromatin, one or more accessible regions can be generated as described in U.S. Pat. Nos. 7,785,792 and 8,071,370. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3) (Cordingley et al. (1987) *Cell* 48:261-270; Pina et al. (1990) *Cell* 60:719-731; and Cirillo et al. (1998) *EMBO J.* 17:244-254).

The fusion molecule may be formulated with a pharmaceutically acceptable carrier, as is known to those of skill in the art. See, for example, Remington's Pharmaceutical Sciences, 17th ed., 1985; and U.S. Pat. Nos. 6,453,242 and 6,534,261.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Additional exemplary functional domains are disclosed, for example, in U.S. Pat. Nos. 6,534,261 and 6,933,113.

Functional domains that are regulated by exogenous small molecules or ligands may also be selected. For example, RheoSwitch® technology may be employed wherein a functional domain only assumes its active conformation in the presence of the external RheoChem™ ligand (see for example US 20090136465). Thus, the ZFP may be operably linked to the regulatable functional domain wherein the resultant activity of the ZFP-TF is controlled by the external ligand.

Nucleases

In certain embodiments, the fusion molecule comprises a DNA-binding binding domain associated with a cleavage (nuclease) domain. As such, gene modification can be achieved using a nuclease, for example an engineered nuclease. Engineered nuclease technology is based on the engineering of naturally occurring DNA-binding proteins. For example, engineering of homing endonucleases with tailored DNA-binding specificities has been described. Chames et al. (2005) Nucleic Acids Res 33(20):e178; Arnould et al. (2006) *J. Mol. Biol.* 355:443-458. In addition, engineering of ZFPs has also been described. See, e.g., U.S. Pat. Nos. 6,534,261; 6,607,882; 6,824,978; 6,979,539; 6,933,113; 7,163,824; and 7,013,219.

In addition, ZFPs and/or TALEs can be fused to nuclease domains to create ZFNs and TALENs—a functional entity that is able to recognize its intended nucleic acid target through its engineered (ZFP or TALE) DNA binding domain and cause the DNA to be cut near the DNA binding site via the nuclease activity.

Thus, the methods and compositions described herein are broadly applicable and may involve any nuclease of interest. Non-limiting examples of nucleases include meganucleases, TALENs and zinc finger nucleases. The nuclease may comprise heterologous DNA-binding and cleavage domains (e.g., zinc finger nucleases; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

In any of the nucleases described herein, the nuclease can comprise an engineered TALE DNA-binding domain and a nuclease domain (e.g., endonuclease and/or meganuclease domain), also referred to as TALENs. Methods and compositions for engineering these TALEN proteins for robust, site specific interaction with the target sequence of the user's choosing have been published (see U.S. Pat. No. 8,586,526). In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) *Nucl Acid Res:* 1-13, doi: 10.1093/nar/gkt1224). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al (2013) *Nat Comm:* 1-8 DOI: 10.1038/ncomms2782). Any TALENs may be used in combination with additional TALENs (e.g., one or more TALENs (cTALENs or FokI-TALENs) with one or more mega-TALs) or other DNA cleavage enzymes.

In certain embodiments, the nuclease comprises a meganuclease (homing endonuclease) or a portion thereof that exhibits cleavage activity. Naturally-occurring meganucleases recognize 15-40 base-pair cleavage sites and are commonly grouped into four families: the LAGLIDADG family ("LAGLIDADG" disclosed as SEQ ID NO: 122), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420, 032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

DNA-binding domains from naturally-occurring meganucleases, primarily from the LAGLIDADG family ("LAGLIDADG" disclosed as SEQ ID NO: 122), have been used to promote site-specific genome modification in plants, yeast, Drosophila, mammalian cells and mice, but this approach has been limited to the modification of either homologous genes that conserve the meganuclease recognition sequence (Monet et al. (1999), *Biochem. Biophysics. Res. Common.* 255: 88-93) or to pre-engineered genomes into which a recognition sequence has been introduced (Route et al. (1994), *Mol. Cell. Biol.* 14: 8096-106; Chilton et al. (2003), *Plant Physiology.* 133: 956-65; Puchta et al. (1996), *Proc. Natl. Acad. Sci. USA* 93: 5055-60; Rong et al. (2002), *Genes Dev.* 16: 1568-81; Gouble et al. (2006), *J. Gene Med.* 8(5):616-622). Accordingly, attempts have been made to engineer meganucleases to exhibit novel binding specificity at medically or biotechnologically relevant sites (Porteus et al. (2005), *Nat. Biotechnol.* 23: 967-73; Sussman et al. (2004), *J. Mol. Biol.* 342: 31-41; Epinat et al. (2003), *Nucleic Acids Res.* 31: 2952-62; Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication Nos. 20070117128; 20060206949; 20060153826; 20060078552; and 20040002092). In addition, naturally-occurring or engineered DNA-binding domains from meganucleases can be operably linked with a cleavage domain from a heterologous nuclease (e.g., FokI) and/or cleavage domains from meganucleases can be operably linked with a heterologous DNA-binding domain (e.g., ZFP or TALE).

In other embodiments, the nuclease is a zinc finger nuclease (ZFN) or

TALE DNA binding domain-nuclease fusion (TALEN). ZFNs and TALENs comprise a DNA binding domain (zinc finger protein or TALE DNA binding domain) that has been engineered to bind to a target site in a gene of choice and cleavage domain or a cleavage half-domain (e.g., from a restriction and/or meganuclease as described herein).

As described in detail above, zinc finger binding domains and TALE DNA binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain or TALE protein can have a novel binding specificity, compared to a naturally-occurring protein. Engineering methods include, but are not limited to, rational design and various types of selection. Rational design includes, for example, using databases comprising triplet (or quadruplet)

nucleotide sequences and individual zinc finger or TALE amino acid sequences, in which each triplet or quadruplet nucleotide sequence is associated with one or more amino acid sequences of zinc fingers or TALE repeat units which bind the particular triplet or quadruplet sequence. See, for example, U.S. Pat. Nos. 6,453,242 and 6,534,261, incorporated by reference herein in their entireties.

Selection of target sites; and methods for design and construction of fusion proteins (and polynucleotides encoding same) are known to those of skill in the art and described in detail in U.S. Pat. Nos. 7,888,121 and 8,409,861, incorporated by reference in their entireties herein.

In addition, as disclosed in these and other references, zinc finger domains, TALEs and/or multi-fingered zinc finger proteins may be linked together using any suitable linker sequences, including for example, linkers of 5 or more amino acids in length. See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. See, also, U.S. Pat. No. 8,772,453.

Thus, nucleases such as ZFNs, TALENs and/or meganucleases can comprise any DNA-binding domain and any nuclease (cleavage) domain (cleavage domain, cleavage half-domain). As noted above, the cleavage domain may be heterologous to the DNA-binding domain, for example a zinc finger or TAL-effector DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, MA; and Belfort et al. (1997) Nucleic Acids Res. 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites, but may lie 1 or more kilobases away from the cleavage site, including between 1-50 base pairs (or any value therebetween including 1-5, 1-10, and 1-20 base pairs), 1-100 base pairs (or any value therebetween), 100-500 base pairs (or any value therebetween), 500 to 1000 base pairs (or any value therebetween) or even more than 1 kb from the cleavage site.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 7,914,796; 8,034,598 and 8,623,618; and U.S. Patent Publication No. 20110201055, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Pat. Nos. 7,914,796 and 8,034,598, the disclosures of which are incorporated by reference in their entireties for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. Nos. 7,914,796; 8,034,598 and 8,623,618, the disclosures of which are incorporated by reference in its entirety for all purposes. In other embodiments, the engineered cleavage half domain comprises the "Sharkey" and/or "Sharkey" mutations (see Guo et al, (2010) J Mol. Biol. 400(1):96-107).

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases (e.g., ZFNs and/or TALENs) can be screened for activity prior to use, for example in a yeast-based chromosomal system as described in as described in U.S. Pat. No. 8,563,314.

In certain embodiments, the nuclease comprises a CRISPR/Cas system. The CRISPR (clustered regularly interspaced short palindromic repeats) locus, which encodes RNA components of the system, and the Cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Exemplary CRISPR/Cas nuclease systems targeted to TCR genes and other genes are disclosed for example, in U.S. Publication No. 20150056705. The nuclease(s) may make one or more double-stranded and/or single-stranded cuts in the target site. In certain embodiments, the nuclease comprises a catalytically inactive cleavage domain (e.g., FokI and/or Cas protein). See, e.g., U.S. Pat. Nos. 9,200,266; 8,703,489 and Guillinger et al. (2014) *Nature Biotech.* 32(6):577-582. The catalytically inactive cleavage domain may, in combination with a catalytically active domain act as a nickase to make a single-stranded cut. Therefore, two nickases can be used in combination to make a double-stranded cut in a specific region. Additional nickases are also known in the art, for example, McCaffery et al. (2016) *Nucleic Acids Res.* 44(2):e11. doi: 10.1093/nar/gkv878. Epub 2015 Oct. 19.

Delivery

The proteins (e.g., transcription factors, nucleases, TCR and CAR molecules), polynucleotides and/or compositions comprising the proteins and/or polynucleotides described herein may be delivered to a target cell by any suitable means, including, for example, by injection of the protein and/or mRNA components. In some embodiments, the proteins are introduced into the cell by cell squeezing (see Kollmannsperger et al (2016) *Nat Comm* 7, 10372 doi: 10.1038/ncomms10372).

Suitable cells include but not limited to eukaryotic and prokaryotic cells and/or cell lines. Non-limiting examples of such cells or cell lines generated from such cells include T-cells, COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as Saccharomyces, Pichia and Schizosaccharomyces. In certain embodiments, the cell line is a CHO-K1, MDCK or HEK293 cell line. Suitable cells also include stem cells such as, by way of example, embryonic stem cells, induced pluripotent stem cells (iPS cells), hematopoietic stem cells, neuronal stem cells and mesenchymal stem cells.

Methods of delivering proteins comprising DNA-binding domains as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

DNA binding domains and fusion proteins comprising these DNA binding domains as described herein may also be delivered using vectors containing sequences encoding one or more of the DNA-binding protein(s). Additionally, additional nucleic acids (e.g., donors) also may be delivered via these vectors. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more DNA-binding protein-encoding sequences and/or additional nucleic acids as appropriate. Thus, when one or more DNA-binding proteins as described herein are introduced into the cell, and additional DNAs as appropriate, they may be carried on the same vector or on different vectors. When multiple vectors are used, each vector may comprise a sequence encoding one or multiple DNA-binding proteins and additional nucleic acids as desired.

Conventional viral and non-viral based gene transfer methods can be used to introduce nucleic acids encoding engineered DNA-binding proteins in cells (e.g., mammalian cells) and target tissues and to co-introduce additional nucleotide sequences as desired. Such methods can also be used to administer nucleic acids (e.g., encoding DNA-binding proteins and/or donors) to cells in vitro. In certain embodiments, nucleic acids are administered for in vivo or ex vivo gene therapy uses. Non-viral vector delivery systems include DNA plasmids, naked nucleic acid, and nucleic acid complexed with a delivery vehicle such as a liposome, lipid nanoparticle or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357: 455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, lipid nanoparticles, immunoliposomes, polycation or lipid:nucleic acid conjugates, naked DNA, mRNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074, 596 and 8,153,773, incorporated by reference herein.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386, 4,946,787; and U.S. Pat. No. 4,897,355) and lipofection reagents are sold commercially (e.g., Transfectam™, Lipofectin™, and Lipofectamine™ RNAiMAX). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485, 054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7) p. 643).

The use of RNA or DNA viral based systems for the delivery of nucleic acids encoding engineered DNA-binding proteins, and/or donors (e.g. CARs or ACTRs) as desired takes advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, retroviral, lentivirus, adenoviral, adeno-associated, vaccinia and herpes simplex virus vectors for gene transfer.

Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS USA* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS USA* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAVS, AAV6, AAV8, AAV8.2, AAV9 and AAVrh10 and pseudo-typed AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. In addition, AAV can be manufactured using a baculovirus system (see e.g. U.S. Pat. Nos. 6,723,551 and 7,271,002).

Purification of AAV particles from a 293 or baculovirus system typically involves growth of the cells which produce the virus, followed by collection of the viral particles from the cell supernatant or lysing the cells and collecting the virus from the crude lysate. AAV is then purified by methods known in the art including ion exchange chromatography (e.g. see U.S. Pat. Nos. 7,419,817 and 6,989,264), ion exchange chromatography and CsC1 density centrifugation (e.g. PCT publication WO2011094198A10), immunoaffinity chromatography (e.g. WO2016128408) or purification using AVB Sepharose (e.g. GE Healthcare Life Sciences).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., (*Proc. Natl. Acad. Sci. USA* 92:9747-9751 (1995)), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by re-implantation of the cells into a patient, usually after selection for cells which have incorporated the vector.

Ex vivo cell transfection for diagnostics, research, transplant or for gene therapy (e.g., via re-infusion of the transfected cells into the host organism) is well known to those of skill in the art. In a preferred embodiment, cells are isolated from the subject organism, transfected with a DNA-binding proteins nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+

(T cells), CD45+ (panB cells), GR-1 (granulocytes), and Tad (differentiated antigen presenting cells) (see Inaba et al., *J. Exp. Med.* 176:1693-1702 (1992)).

Stem cells that have been modified may also be used in some embodiments. For example, neuronal stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific ZFNs (see, U.S. patent Publication No. 20100003756) in the stem cells, or those that are disrupted in a caspase, again using caspase-6 specific ZFNs for example. These cells can be transfected with the ZFP TFs that are known to regulate TCR.

Vectors (e.g., retroviruses, adenoviruses, liposomes, etc.) containing therapeutic DNA-binding proteins (or nucleic acids encoding these proteins) can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) J. Virol. 72:8463-8471; Zuffery et al. (1998) J. Virol. 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells, including T-cells and stem cells of any type. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces*, *Pichia* and *Schizosaccharomyces*. Progeny, variants and derivatives of these cell lines can also be used.

Applications

The disclosed compositions and methods can be used for any application in which it is desired to modulate TCR expression and/or functionality, including but not limited to, therapeutic and research applications in which TCR modulation is desirable. For example, the disclosed compositions can be used in vivo and/or ex vivo (cell therapies) to disrupt the expression of endogenous TCRs in T cells modified for adoptive cell therapy to express one or more exogenous CARs, exogenous TCRs, or other cancer-specific receptor molecules, thereby treating and/or preventing the cancer. In addition, in such settings, abrogation of TCR expression within a cell can eliminate or substantially reduce the risk of an unwanted cross reaction with healthy, nontargeted tissue (i.e. a graft-vs-host response).

Methods and compositions also include stem cell compositions wherein the TCRA and/or TCRB genes within the stem cells has been modulated (modified) and the cells further comprise an ACTR and/or a CAR and/or an isolated or engineered TCR. For example, TCR knock out or knock down modulated allogeneic hematopoietic stem cells can be introduced into a HLA-matched patient following bone marrow ablation. These altered HSC would allow the re-colonization of the patient but would not cause potential GvHD. The introduced cells may also have other alterations to help during subsequent therapy (e.g., chemotherapy resistance) to treat the underlying disease. The TCR null cells also have use as an "off the shelf" therapy in emergency room situations with trauma patients.

The methods and compositions of the invention are also useful for the design and implementation of in vitro and in vivo models, for example, animal models of TCR or and associated disorders, which allows for the study of these disorders.

All patents, patent applications and publications mentioned herein are hereby incorporated by reference in their entireties.

Although disclosure has been provided in some detail by way of illustration and example for the purposes of clarity and understanding, it will be apparent to those of skill in the art that various changes and modifications can be practiced without departing from the spirit or scope of the disclosure. Accordingly, the foregoing disclosure and following examples should not be construed as limiting.

EXAMPLES

Example 1

Design of TCR-specific Nucleases

TCR-specific ZFNs were constructed to enable site specific introduction of double strand breaks at the TCRα (TCRA) gene. ZFNs were designed essentially as described in Urnov et al. (2005) *Nature* 435(7042):646-651, Lombardo et al (2007) *Nat Biotechnol.* Nov; 25(11):1298-306, and U.S. Patent Publications 2008-0131962, 2015-016495, 2014-0120622, 2014-0301990 and U.S. Pat. No. 8,956,828. The ZFN pairs targeted different sites in the constant region of the TCRA gene (see FIG. 1). The recognition helices for exemplary ZFN pairs as well as the target sequence are shown below in Table 1. Target sites of the TCRA zinc-finger designs are shown in the first column. Nucleotides in the target site that are targeted by the ZFP recognition helices are indicated in uppercase letters; non-targeted nucleotides indicated in lowercase. Linkers used to join the FokI nuclease domain and the ZFP DNA binding domain are also shown (see U.S. Patent Publication 20150132269). For example, the amino acid sequence of the domain linker L0 is DNA binding domain-QLVKS-FokI nuclease domain (SEQ ID NO:5). Similarly, the amino acid sequences for the domain linker N7a is FokI nuclease domain-SGTPHEVGVYTL-DNA binding domain (SEQ ID NO:6), and N7c is FokI nuclease domain-SGAIRCHDEFWF-DNA binding domain (SEQ ID NO:7).

TABLE 1

| TCR-α (TCRA) Zinc-finger Designs | | | | | | | |
|---|---|---|---|---|---|---|---|
| ZFN Name target sequence | F1 | F2 | F3 | F4 | F5 | F6 | Domain linker |
| SBS55204 5'ttGCTC TTGAAGTC cATAGACc tcatgt (SEQ ID NO: 8) | DRSNLSR (SEQ ID NO: 22) | QKVTLAA (SEQ ID NO: 23) | DRSALSR (SEQ ID NO: 24) | TSGNLTR (SEQ ID NO: 25) | YRSSLKE (SEQ ID NO: 26) | TSGNLTR (SEQ ID NO: 25) | L0 |
| SBS53759 5'gtGCTG TGgCCTGG AGCAACAa atctga (SEQ ID NO: 9) | QQNVLIN (SEQ ID NO: 27) | QNATRTK (SEQ ID NO: 28) | QSGHLAR (SEQ ID NO: 29) | NRYDLMT (SEQ ID NO: 30) | RSDSLLR (SEQ ID NO: 31) | QSSDLTR (SEQ ID NO: 32) | L0 |
| SBS55229 5'ctGTTG CTCTTGAA GTCcatag acctca (SEQ ID NO: 10) | DRSALAR (SEQ ID NO: 33) | QSGNLAR (SEQ ID NO: 34) | HRSTLQG (SEQ ID NO: 35) | QSGDLTR (SEQ ID NO: 36) | TSGSLTR (SEQ ID NO: 37) | NA | L0 |

TABLE 1-continued

TCR-α (TCRA) Zinc-finger Designs

| ZFN Name target sequence | F1 | F2 | F3 | F4 | F5 | F6 | Domain linker |
|---|---|---|---|---|---|---|---|
| SBS53785 5'ctGTGG CCtGGAGC AACAaatc tgactt (SEQ ID NO: 11) | QHQVLVR (SEQ ID NO: 38) | QNATRTK (SEQ ID NO: 28) | QSGHLSR (SEQ ID NO: 39) | DRSDLSR (SEQ ID NO: 40) | RSDALAR (SEQ ID NO: 41) | NA | L0 |
| SBS53810 5'agGATT CGGAACCC AATCACtg (SEQ ID NO: 12) | DQSNLRA (SEQ ID NO: 42) | TSSNRKT (SEQ ID NO: 43) | DSSTRKT (SEQ ID NO: 44) | QSGNLAR (SEQ ID NO: 34) | RSDDLSE (SEQ ID NO: 45) | TNSNRKR (SEQ ID NO: 46) | L0 |
| SBS55255 5'ctCCTG AAAGTGGC CGGgttta atctgc (SEQ ID NO: 13) | RSDHLST (SEQ ID NO: 47) | DRSHLAR (SEQ ID NO: 48) | LKQHLNE (SEQ ID NO: 49) | TSGNLTR (SEQ ID NO: 25) | HRTSLTD (SEQ ID NO: 50) | NA | L0 |
| SBS55248 5'agGATT CGGAACCC AATCACtg acaggt (SEQ ID NO: 14) | DQSNLRA (SEQ ID NO: 42) | TSSNRKT (SEQ ID NO: 43) | LQQTLAD (SEQ ID NO: 51) | QSGNLAR (SEQ ID NO: 34) | RREDLIT (SEQ ID NO: 52) | TSSNLSR (SEQ ID NO: 53) | L0 |
| SBS55254 5'ctCCTG AAAGTGGC CGGgttta atctgc (SEQ ID NO: 13) | RSDHLST (SEQ ID NO: 47) | DRSHLAR (SEQ ID NO: 48) | LKQHLNE (SEQ ID NO: 49) | QSGNLAR (SEQ ID NO: 34) | HNSSLKD (SEQ ID NO: 54) | NA | L0 |
| SBS55260 5'ctCCTG AAAGTGGC CGGgttta atctgc (SEQ ID NO: 13) | RSDHLST (SEQ ID NO: 47) | DRSHLAR (SEQ ID NO: 48) | LNHHLQQ (SEQ ID NO: 55) | QSGNLAR (SEQ ID NO: 34) | HKTSLKD (SEQ ID NO: 56) | NA | L0 |
| SBS55266 5'tcAAGC TGGTCGAG aAAAGCTt tgaaac (SEQ ID NO: 15) | QSSDLSR (SEQ ID NO: 57) | QSGNRTT (SEQ ID NO: 58) | RSANLAR (SEQ ID NO: 59) | DRSALAR (SEQ ID NO: 33) | RSDVLSE (SEQ ID NO: 60) | KHSTRRV (SEQ ID NO: 61) | N7c |
| SBS53853 5'aaCAGG TAaGACAG GGGTCTAg cctggg (SEQ ID NO: 16) | TMHQRVE (SEQ ID NO: 62) | TSGHLSR (SEQ ID NO: 63) | RSDHLTQ (SEQ ID NO: 64) | DSANLSR (SEQ ID NO: 65) | QSGSLTR (SEQ ID NO: 66) | AKWNLDA (SEQ ID NO: 67) | L0 |
| SBS53860 5'ctGTGC TAGACATG aGGTCTAt ggactt (SEQ ID NO: 17) | TMHQRVE (SEQ ID NO: 62) | TSGHLSR (SEQ ID NO: 63) | RNDSLKT (SEQ ID NO: 68) | DSSNLSR (SEQ ID NO: 69) | QKATRTT (SEQ ID NO: 70) | RNASRTR (SEQ ID NO: 72) | N7a |

TABLE 1-continued

TCR-α (TCRA) Zinc-finger Designs

| ZFN Name target sequence | F1 | F2 | F3 | F4 | F5 | F6 | Domain linker |
|---|---|---|---|---|---|---|---|
| SBS53863 5'ttCAAG AGCAACAG tGCTGTGg cctgga (SEQ ID NO: 18) | RSDSLLR (SEQ ID NO: 31) | QSSDLRR (SEQ ID NO: 73) | RSDNLSE (SEQ ID NO: 74) | ERANRNS (SEQ ID NO: 75) | RSDNLAR (SEQ ID NO: 76) | QKVNLMS (SEQ ID NO: 77) | L0 |
| SBS55287 5'ttCAAG AGCAACAG tGCTGTGg cctgga (SEQ ID NO: 18) | RSDSLLR (SEQ ID NO: 31) | QSSDLRR (SEQ ID NO: 73) | RSDNLSE (SEQ ID NO: 74) | ERANRNS (SEQ ID NO: 75) | RSDNLAR (SEQ ID NO: 76) | QKVNLRE (SEQ ID NO: 78) | L0 |
| SBS53885 5'ccTGTCAG tGATTGGG TTCCGaat cctc (SEQ ID NO: 19) | RSDTLSE (SEQ ID NO: 79) | TSGSLTR (SEQ ID NO: 37) | RSDHLST (SEQ ID NO: 47) | TSSNRTK (SEQ ID NO: 71) | RSDNLSE (SEQ ID NO: 74) | WHSSLRV (SEQ ID NO: 83) | N7a |
| SBS52774 5'ccTGTC AGtGATTG GGTTCCGa atcctc (SEQ ID NO: 19) | RKQTRTT (SEQ ID NO: 80) | HRSSLRR (SEQ ID NO: 81) | RSDHLST (SEQ ID NO: 47) | TSANLSR (SEQ ID NO: 82) | RSDNLSE (SEQ ID NO: 74) | WHSSLRV (SEQ ID NO: 83) | N7a |
| SBS53909 5'tcCTCC TGAAAGTG GCCGGGtt taatct (SEQ ID NO: 20) | RSAHLSR (SEQ ID NO: 84) | DRSDLSR (SEQ ID NO: 40) | RSDVLSV (SEQ ID NO: 85) | QNNHRIT (SEQ ID NO: 86) | RSDVLSE (SEQ ID NO: 60) | SPSSRRT (SEQ ID NO: 87) | L0 |
| SBS52742 5'tcCTCC TGAAAGTG GCCGGGtt taatct (SEQ ID NO: 20) | RSAHLSR (SEQ ID NO: 84) | DRSDLSR (SEQ ID NO: 40) | RSDSLSV (SEQ ID NO: 88) | QNANRKT (SEQ ID NO: 89) | RSDVLSE (SEQ ID NO: 60) | SPSSRRT (SEQ ID NO: 87) | L0 |
| SBS53856 5'ctGTGC TAGACATG aGGTCTAt g (SEQ ID NO: 21) | TMHQRVE (SEQ ID NO: 62) | TSGHLSR (SEQ ID NO: 63) | RSDSLST (SEQ ID NO: 90) | DRANRIK (SEQ ID NO: 91) | QKATRTT (SEQ ID NO: 70) | RNASRTR (SEQ ID NO: 72) | N7a |

All ZFNs were tested and found to bind to their target sites and found to be active as nucleases.

Guide RNAs for the *S. pyogenes* CRISPR/Cas9 system were also constructed to target the TCRA gene. See, also, U.S. Publication No. 201500566705 for additional TCR alpha-targeted guide RNAs. The target sequences in the TCRA gene are indicated as well as the guide RNA sequences in Table 2 below. All guide RNAs are tested in the CRISPR/Cas9 system and are found to be active.

TABLE 2

Guide RNAs for the constant region of human TCRA (TRAC)

| Name | Strand | Target (5'→3') | gRNA (5' → 3') |
|---|---|---|---|
| TRAC-Gr14 | R | GCTGGTACACGGCAGGGTCAGGG (SEQ ID NO: 92) | GCTGGTACACGGCAGGGTCA (SEQ ID NO: 104) |
| TRAC-Gr25 | R | AGAGTCTCTCAGCTGGTACACGG (SEQ ID NO: 93) | gAGAGTCTCTCAGCTGGTACA (SEQ ID NO: 105) |
| TRAC-Gr71 | R | GAGAATCAAAATCGGTGAATAGG (SEQ ID NO: 94) | GAGAATCAAAATCGGTGAAT (SEQ ID NO: 106) |
| TRAC-Gf155 | F | ACAAAACTGTGCTAGACATGAGG (SEQ ID NO: 95) | gACAAAACTGTGCTAGACATG (SEQ ID NO: 107) |
| TRAC-Gf191 | F | AGAGCAACAGTGCTGTGGCCTGG (SEQ ID NO: 96) | gAGAGCAACAGTGCTGTGGCC (SEQ ID NO: 108) |
| TRAC-Gf271 | F | GACACCTTCTTCCCCAGCCCAGG (SEQ ID NO: 97) | GACACCTTCTTCCCCAGCCC (SEQ ID NO: 109) |
| TRAC-Gr2146 | R | CTCGACCAGCTTGACATCACAGG (SEQ ID NO: 98) | gCTCGACCAGCTTGACATCAC (SEQ ID NO: 110) |
| TRAC-Gf2157 | F | AAGTTCCTGTGATGTCAAGCTGG (SEQ ID NO: 99) | gAAGTTCCTGTGATGTCAAGC (SEQ ID NO: 111) |
| TRAC-Gf2179 | F | GTCGAGAAAAGCTTTGAAACAGG (SEQ ID NO: 100) | GTCGAGAAAAGCTTTGAAAC (SEQ ID NO: 112) |
| TRAC-Gr3081 | R | TTCGGAACCCAATCACTGACAGG (SEQ ID NO: 101) | gTTCGGAACCCAATCACTGAC (SEQ ID NO: 113) |
| TRAC-Gr3099 | R | CCACTTTCAGGAGGAGGATTCGG (SEQ ID NO: 102) | gCCACTTTCAGGAGGAGGATT (SEQ ID NO: 114) |
| TRAC-Gr3105 | R | ACCCGGCCACTTTCAGGAGGAGG (SEQ ID NO: 103) | gACCCGGCCACTTTCAGGAGG (SEQ ID NO: 115) |

Thus, the nucleases described herein (e.g., nucleases comprising a ZFP or a sgRNA DNA-binding domain) bind to their target sites and cleave the TCRA gene, thereby making genetic modifications within a TCRA gene comprising any of SEQ ID NO:6-48 or 137-205, including modifications (insertions and/or deletions) within any of these sequences (SEQ ID NO:8-21 and/or 92-103) and/or modifications within the following sequences: AACAGT, AGTGCT, CTCCT, TTGAAA, TGGACTT and/or AATCCTC (see, FIG. 1B). TALE nucleases targeted to these target sites are also designed and found to be functional in terms of binding and activity.

Furthermore, the DNA-binding domains (ZFPs and sgRNAs) all bound to their target sites and ZFP, TALE and sRNA DNA-binding domains that recognize these target sites are also formulated into active engineered transcription factors when associated with one or more transcriptional regulatory domains.

Example 2

Nuclease Activity in Vitro

The ZFNs described in Table 1 were used to test nuclease activity in K562 cells. To test cleavage activity, plasmids encoding the pairs of human TCRA-specific ZFNs described above were transfected into K562 cells with plasmid or mRNAs. K562 cells were obtained from the American Type Culture Collection and grown as recommended in RPMI medium (Invitrogen) supplemented with 10% qualified fetal bovine serum (FBS, Cyclone). For transfection, ORFs for the active nucleases listed in Table 1 were cloned into an expression vector optimized for mRNA production bearing a 5' and 3' UTRs and a synthetic polyA signal. The mRNAs were generated using the mMessage mMachine T7 Ultra kit (Ambion) following the manufacturer's instructions. In vitro synthesis of nuclease mRNAs used either a pVAX-based vector containing a T7 promoter, the nuclease proper and a polyA motif for enzymatic addition of a polyA tail following the in vitro transcription reaction, or a pGEM based vector containing a T7 promoter, a 5'UTR, the nuclease proper, a 3'UTR and a 64 bp polyA stretch, or a PCR amplicon containing a T7 promoter, a 5'UTR, the nuclease proper, a 3'UTR and a 60 bp polyA stretch. One million K562 cells were mixed with 250 ng or 500 ng of the ZFN encoding mRNA. Cells were transfected in an Amaxa Nucleofector IITM using program T-16 and recovered into 1.4 mL warm RPMI medium +10% FBS. Nuclease activity was assessed by deep sequencing (MiSeq, Illumina) as per standard protocols three days following transfection. The results are presented below in Table 3.

TABLE 3

Zinc Finger Nuclease activity

| Pair # | ZFN pair | NHEJ % (250 ng/ZFN) | SD | NHEJ % (500 ng/ZFN) | SD | Site |
|---|---|---|---|---|---|---|
| 1 | 55204:53759 | 76.7 | 1.3 | 87.7 | 1 | A2 |
| 2 | 55229:53785 | 91.4 | 1.5 | 93.6 | 1.7 | B |
| 3 | 53810:55255 | 81.6 | 0.6 | 91.5 | 1.3 | D1 |
| 4 | 55248:55254 | 95.4 | 1.8 | 96.2 | 1.2 | D2 |
| 5 | 55248:55260 | 87.9 | 1.3 | 93.0 | 1 | D3 |
| 6 | 55266:53853 | 85.3 | 1.4 | 88.9 | 0.4 | E |
| 7 | 53860:53863 | 77.1 | 1.7 | 87.3 | 1.1 | F1 |
| 8 | 53856:55287 | 53.6 | 3.2 | 74.8 | 1.3 | F2 |
| 9 | 53885:53909 | 90.1 | 1.6 | 90.2 | 1.5 | G1 |
| 10 | 52774:52742 | 76.8 | 0.8 | 84.4 | 2.2 | G0 |
| 11 | GFP | 0 | | 0 | | |

Highly active TCRA specific TALENs have also been previously described (see WO2014153470).

The human TCRA-specific CRISPR/Cas9 systems were also tested. The activity of the CRISPR/Cas9 systems in human K562 cells was measured by MiSeq analysis. Cleavage of the endogenous TCRA DNA sequence by Cas9 is assayed by high-throughput sequencing (Miseq, Illumina).

In these experiments, Cas9 was supplied on a pVAX plasmid, and the sgRNA is supplied on a plasmid under the control of a promoter (e.g., the U6 promoter or a CMV promoter). The plasmids were mixed at either 100 ng of each or 400 ng of each and were mixed with 2e5 cells per run. The cells were transfected using the Amaxa system. Briefly, an Amaxa transfection kit is used and the nucleic acids are transfected using a standard Amaxa shuttle protocol. Following transfection, the cells are let to rest for 10 minutes at room temperature and then resuspended in prewarmed RPMI. The cells are then grown in standard conditions at 37° C. Genomic DNA was isolated 7 days after transfection and subject to MiSeq analysis.

Briefly, the guide RNAs listed in Table 2 were tested for activity. The guide RNAs were tested in three different configurations: G0 is the set up described above. G1 used a pVAX vector comprising a CMV promoter driving expression of the Cas9 gene and a U6-Guide RNA-tracer expression cassette where transcription of both reading frames is in the same orientation. G2 is similar to G1 except that the Cas9 and U6-Guide expression cassettes are in opposite orientations. These three set ups were tested using either 100 ng or 400 ng of transfected DNA, and the results are presented below in Table 4. Results are expressed as the 'percent indels' or "NHEJ %', where 'indels' means small insertions and/or deletions found as a result of the error prone NHEJ repair process at the site of a nuclease-induced double strand cleavage.

TABLE 4

CRISPR/Cas activity

% total_indels

| | GR0 | | GR1 | | GR2 | |
|---|---|---|---|---|---|---|
| Guide used | NHEJ % (100 ng) | NHEJ % (400 ng) | NHEJ % (100 ng) | NHEJ % (400 ng) | NHEJ % (100 ng) | NHEJ % (400 ng) |
| TCRA-Gr14 | 6.4 | 25.8 | 0.6 | 12.4 | 0.5 | 10.2 |
| TCRA-Gr25 | 14.6 | 26.9 | 2.4 | 21.7 | 1.1 | 21.6 |
| TCRA-Gr71 | 3.7 | 13.8 | 0.3 | 4.2 | 0.3 | 7.8 |
| TCRA-Gf155 | 6.0 | 19.5 | 1.2 | 12.7 | 0.8 | 15.9 |
| TCRA-Gf191 | 1.0 | 6.9 | 0.3 | 2.3 | 0.4 | 4.5 |
| TCRA-Gf271 | 4.7 | 21.5 | 0.8 | 10.3 | 0.7 | 15.2 |
| TCRA-Gr2146 | 1.1 | 8.8 | 0.3 | 1.7 | 0.2 | 2.0 |
| TCRA-Gf2157 | 3.8 | 22.2 | 0.6 | 9.6 | 0.6 | 12.0 |
| TCRA-Gf2179 | 0.8 | 4.9 | 0.2 | 1.8 | 0.2 | 1.4 |
| TCRA-Gr3081 | 5.9 | 23.6 | 0.7 | 11.5 | 0.8 | 12.6 |
| TCRA-Gr3099 | 2.1 | 21.1 | 0.4 | 7.1 | 0.3 | 6.2 |
| TCRA-Gr3105 | 12.1 | 45.9 | 2.2 | 22.0 | 1.0 | 7.6 |
| ZFN controls | | | | | | |
| 55248:55254 | 24.2 | 52.4 | | | | |
| 55229:53785 | 6.0 | 24.5 | | | | |
| 55266:53853 | 12.0 | 37.0 | | | | |

As shown, the nucleases described herein induce cleavage and genomic modifications at the targeted site.

Thus, the nucleases described herein (e.g., nucleases comprising a ZFP, a TALE or a sgRNA DNA-binding domain) bind to their target sites and cleave the TCRA gene, thereby making genetic modifications within a TCRA gene comprising any of SEQ ID NO:8-21 or 92-103, including modifications (insertions and/or deletions) within any of these sequences (SEQ ID NO:8-21, 92-103); modifications within 1-50 (e.g., 1 to 10) base pairs of these gene sequences; modifications between target sites of paired target sites (for dimers); and/or modifications within one or more of the following sequences: AACAGT, AGTGCT, CTCCT, TTGAAA, TGGACTT and/or AATCCTC (see, FIG. 1B).

Furthermore, the DNA-binding domains (ZFPs, TALEs and sgRNAs) all bound to their target sites and are also formulated into active engineered transcription factors when associated with one or more transcriptional regulatory domains.

Example 3

TCRA-specific ZFN Activity in T Cells

The TCRA-specific ZFN pairs were also tested in human T cells for nuclease activity. mRNAs encoding the ZFNs were transfected into purified T cells.

Briefly, T cells were obtained from leukopheresis product and purified using the Miltenyi CliniMACS system (CD4 and CD8 dual selection). These cells were then activated using Dynabeads (ThermoFisher) according to manufacturer's protocol. 3 days post activation, the cells were transfected with three doses of mRNA (60, 120 and 250 μg/mL) using a Maxcyte electroporator (Maxcyte), OC-100, 30e6 cells/mL, volume of 0.1 mL. Cells were analyzed for on target TCRA modification using deep sequencing (Miseq, Illumina) at 10 days after transfection. Cell viability and cell growth (total cell doublings) were measured throughout the 13-14 days of culture. In addition, TCR on the cell surface of the treated cells was measured using standard FACS analysis at day 10 of culture staining for CD3.

Figure 2B:
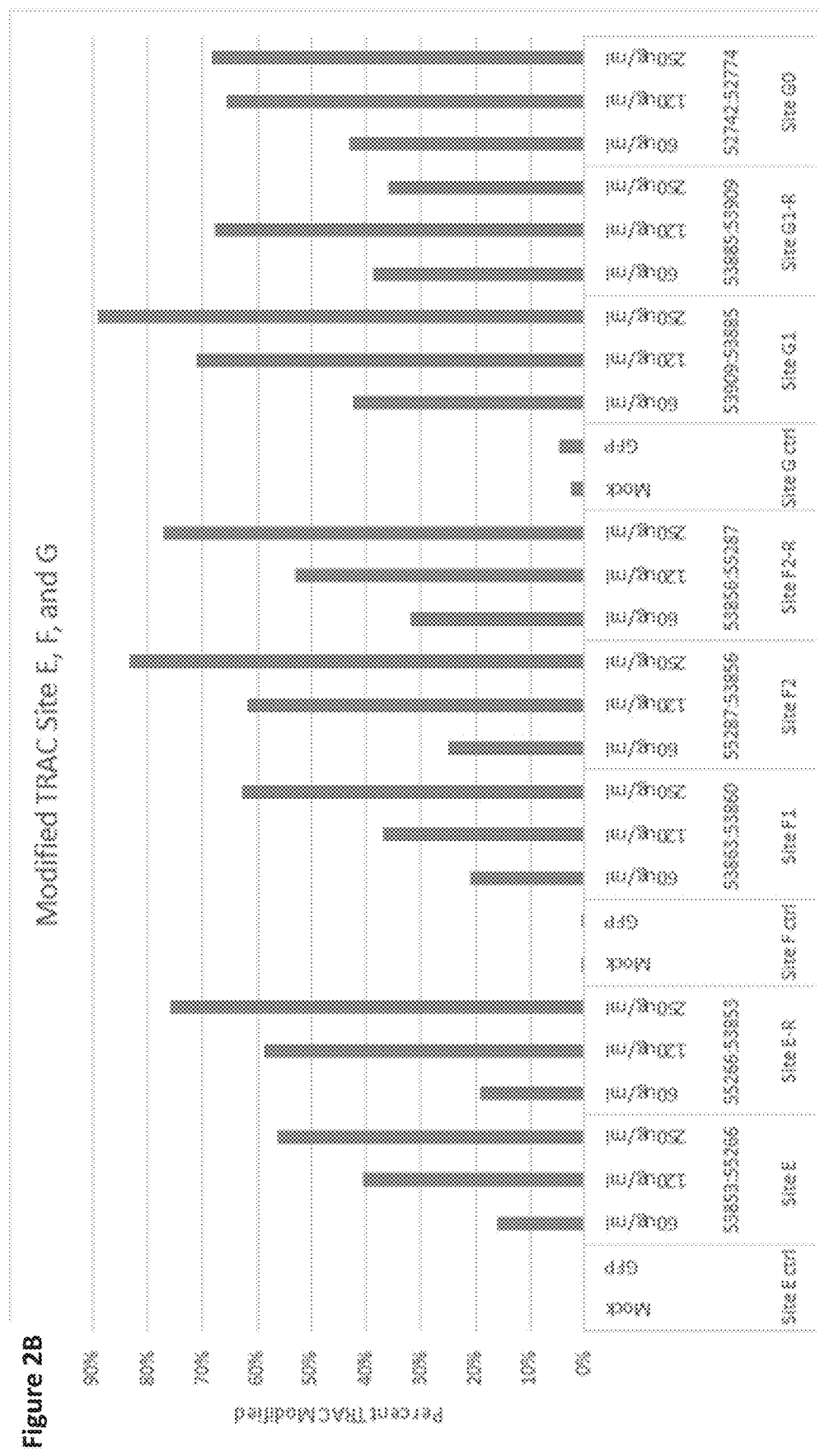
Figure 3:
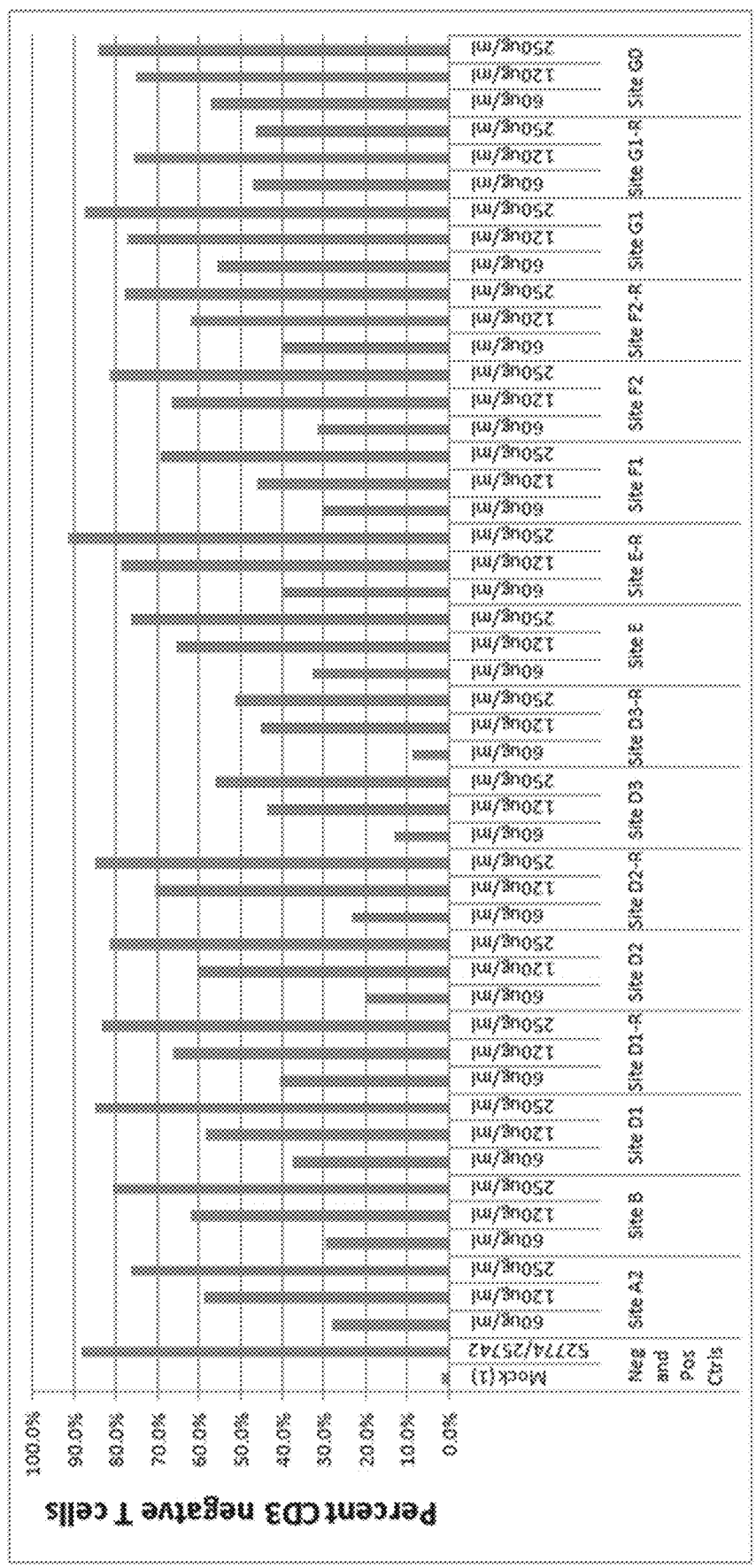
FIG. 3 depicts the percent of CD3 negative T cells following treatment with the TCRA-specific ZFN pairs as analyzed by FACS analysis.
Figure 4:
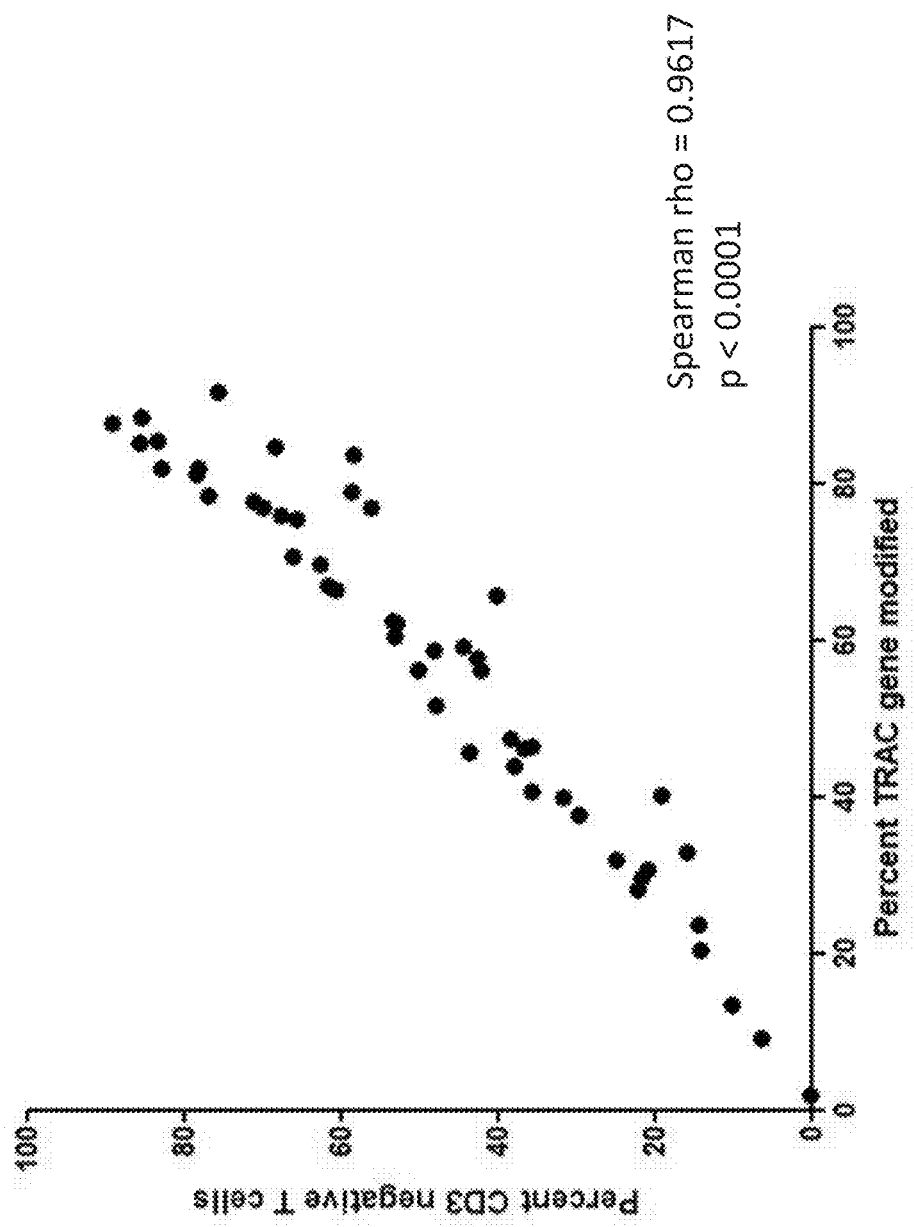
FIG. 4 is a graph showing the high degree of correlation in T cells between levels of TCRA sequence modification as measured via high throughput sequencing and loss of CD3 expression as measured by fluorescence activated cell sorting.

The TCRA-specific ZFN pairs were all active in T cells and some were capable of causing more than 80% TCRA allele modification in these conditions (see FIGS. 2A and 2B). Similarly, T cells treated with the ZFNs lost expression of CD3, where FACS analysis showed that in some cases between 80 and 90% of the T cells were CD3 negative (FIG. 3). A comparison between percent TCRA modified by ZFN and CD3 loss in these cells demonstrated a high degree of correlation (FIG. 4). Cell viability was comparable to the mock treatment controls, and TCRA knockout cell growth was also comparable to the controls (see FIG. 5A-5D).

Example 4

Double Knockout of B2M and TCRA with Targeted Integration

Nucleases as described above and B2M targeted nuclease described in Table 5 (see, also U.S. Publication No. 20170173080) were used to inactivate B2M and TCRA and to introduce, via targeted integration, a donor (transgene) into either the TCRA or B2M locus. The B2M specific ZFNs are shown below in Table 5:

(b) Group 2 (TCRA and B2M ZFNs and donor with TCRA homology arms): TCRA 120 ug/mL; B2M 60 ug/mL and AAV (TCRA-Site E-hPGK-eGFP-Clone E2) 1E5 vg/cell;
(c) Group 3 (TCRA and B2M ZFNs and donor with TCRA homology arms): TCRA 120 ug/mL; B2M 60 ug/mL; and AAV (TCRA-Site E-hPGK-eGFP-Clone E2) 3E4 vg/cell;
(d) Group 4 (TCRA and B2M ZFNs and donor with B2M homology arms): TCRA 120 ug/mL; B2M 60 ug/mL and AAV (pAAV B2M-hPGK GFP) 1E5 vg/cell
(e) Group 5 (TCRA and B2M ZFNs and donor with B2M homology arms): TCRA 120 ug/mL; B2M 60 ug/mL and AAV (pAAV B2M-hPGK GFP) 3E4 vg/cell. All experiments were conducted at 3e7 cells/ml cell density using the protocol as described in U.S. application Ser. No. 15/347,182 (extreme cold shock) and were cultured to cold shock at 30° C. overnight post electroporation.

The following day (day 4), cells were diluted to 0.5e6 cells/ml and transferred to cultures at 37° C. Three days later (day 7), cells diluted to 0.5e6 cells/ml again. After three and seven more days in culture (days 10 and 14, respectively), cells were harvested for FACS and MiSeq analysis (diluted to 0.5e6 cells/ml).

As shown in FIG. 6, GFP expression indicated that target integration was successful and that genetically modified cells comprising B2M and TCRA modifications (insertions and/or deletions) within the nuclease target sites (or within 1 to 50, 1-20, 1-10 or 1-5 base pairs of the nuclease target sites), including within the TTGAAA and TCAAAT (between the paired target sites) as disclosed herein were obtained.

TABLE 5

B2M-specific ZFN designs

| ZFN Name target sequence | F1 | F2 | F3 | F4 | F5 | F6 | Domain linker |
|---|---|---|---|---|---|---|---|
| SBS57327 5' taGCAATTC AGGAAaTTT GACtttcca t (SEQ ID NO: 123) | DRSNLSR (SEQ ID NO: 22) | ARWYLDK (SEQ ID NO: 125) | QSGNLAR (SEQ ID NO: 34) | AKWNLDA (SEQ ID NO: 67) | QQHVLQN (SEQ ID NO: 119) | QNATRTK (SEQ ID NO: 28) | L0 |
| SBS57332 5'tgTCGGA TgGATGAAA CCCAGacac ata (SEQ ID NO: 124) | RSDNLSE (SEQ ID NO: 74) | ASKTRTN (SEQ ID NO: 120) | QSGNLAR (SEQ ID NO: 34) | TSANLSR (SEQ ID NO: 82) | TSGNLTR (SEQ ID NO: 25) | RTEDRLA (SEQ ID NO: 121) | N6a |

In this experiment, the TCRA-specific ZFN pair was SBS#55266/SBS#53853, comprising the sequence TTGAAA between the TCRA-specific ZFN target sites (Table 1), and the B2M pair was SBS#57332/SBS#57327 (Table 5), comprising the sequence TCAAAT between the B2M-specific ZFN target sites.

Briefly, T-Cells (AC-TC-006) were thawed and activated with CD3/28 dynabeads (1:3 cells:bead ratio) in X-vivo15 T-cell culture media (day 0). After two days in culture (day 2), an AAV donor (comprising a GFP transgene and homology arms to the TCRA or B2M gene) was added to the cell culture, except control groups without donor were also maintained. The following day (day 3), TCRA and B2M ZFNs were added via mRNA delivery in the following 5 Groups:
(a) Group 1 (TCRA and B2M ZFNs only, no donor): TCRA 120 ug/mL: B2M only 60 ug/mL;

Experiments are also performed in which a CAR transgene is integrated into the B2M and/or TCRA locus to created double B2M/TCRA knockouts that express a CAR.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing description and examples should not be construed as limiting.

What is claimed is:

1. A fusion molecule comprising a DNA-binding domain that binds to exon c1, c2 or c3 of the TCRA gene and a transcriptional regulatory domain or a nuclease domain, wherein the DNA-binding domain comprises: a zinc finger protein (ZFP) comprising 5 or 6 zinc finger domains designated F1 to F5 or F1 to F6, each zinc finger domain comprising a recognition helix region as shown in a single row of the following Table:

| ZFN Name | F1 | F2 | F3 | F4 | F5 | F6 |
|---|---|---|---|---|---|---|
| SBS55204 | DRSNLSR (SEQ ID NO: 22) | QKVTLAA (SEQ ID NO: 23) | DRSALSR (SEQ ID NO: 24) | TSGNLTR (SEQ ID NO: 25) | YRSSLKE (SEQ ID NO: 26) | TSGNLTR (SEQ ID NO: 25) |
| SBS53759 | QQNVLIN (SEQ ID NO: 27) | QNATRTK (SEQ ID NO: 28) | QSGHLAR (SEQ ID NO: 29) | NRYDLMT (SEQ ID NO: 30) | RSDSLLR (SEQ ID NO: 31) | QSSDLTR (SEQ ID NO: 32) |
| SBS55229 | DRSALAR (SEQ ID NO: 33) | QSGNLAR (SEQ ID NO: 34) | HRSTLQG (SEQ ID NO: 35) | QSGDLTR (SEQ ID NO: 36) | TSGSLTR (SEQ ID NO: 37) | NA |
| SBS53785 | QHQVLVR (SEQ ID NO: 38) | QNATRTK (SEQ ID NO: 28) | QSGHLSR (SEQ ID NO: 39) | DRSDLSR (SEQ ID NO: 40) | RSDALAR (SEQ ID NO: 41) | NA |
| SBS53810 | DQSNLRA (SEQ ID NO: 42) | TSSNRKT (SEQ ID NO: 43) | DSSTRKT (SEQ ID NO: 44) | QSGNLAR (SEQ ID NO: 34) | RSDDLSE (SEQ ID NO: 45) | TNSNRKR (SEQ ID NO: 46) |
| SBS55255 | RSDHLST (SEQ ID NO: 47) | DRSHLAR (SEQ ID NO: 48) | LKQHLNE (SEQ ID NO: 49) | TSGNLTR (SEQ ID NO: 25) | HRTSLTD (SEQ ID NO: 50) | NA |
| SBS55248 | DQSNLRA (SEQ ID NO: 42) | TSSNRKT (SEQ ID NO: 43) | LQQTLAD (SEQ ID NO: 51) | QSGNLAR (SEQ ID NO: 34) | RREDLIT (SEQ ID NO: 52) | TSSNLSR (SEQ ID NO: 53) |
| SBS55254 | RSDHLST (SEQ ID NO: 47) | DRSHLAR (SEQ ID NO: 48) | LKQHLNE (SEQ ID NO: 49) | QSGNLAR (SEQ ID NO: 34) | HNSSLKD (SEQ ID NO: 54) | NA |

-continued

| ZFN Name | F1 | F2 | F3 | F4 | F5 | F6 |
|---|---|---|---|---|---|---|
| SBS55260 | RSDHLST (SEQ ID NO: 47) | DRSHLAR (SEQ ID NO: 48) | LNHHLQQ (SEQ ID NO: 55) | QSGNLAR (SEQ ID NO: 34) | HKTSLKD (SEQ ID NO: 56) | NA |
| SBS55266 | QSSDLSR (SEQ ID NO: 57) | QSGNRTT (SEQ ID NO: 58) | RSANLAR (SEQ ID NO: 59) | DRSALAR (SEQ ID NO: 33) | RSDVLSE (SEQ ID NO: 60) | KHSTRRV (SEQ ID NO: 61) |
| SBS53853 | TMHQRVE (SEQ ID NO: 62) | TSGHLSR (SEQ ID NO: 63) | RSDHLTQ (SEQ ID NO: 64) | DSANLSR (SEQ ID NO: 65) | QSGSLTR (SEQ ID NO: 66) | AKWNLDA (SEQ ID NO: 67) |
| SBS53860 | TMHQRVE (SEQ ID NO: 62) | TSGHLSR (SEQ ID NO: 63) | RNDSLKT (SEQ ID NO: 68) | DSSNLSR (SEQ ID NO: 69) | QKATRTT (SEQ ID NO: 70) | RNASRTR (SEQ ID NO: 72) |
| SBS53863 | RSDSLLR (SEQ ID NO: 31) | QSSDLRR (SEQ ID NO: 73) | RSDNLSE (SEQ ID NO: 74) | ERANRNS (SEQ ID NO: 75) | RSDNLAR (SEQ ID NO: 76) | QKVNLMS (SEQ ID NO: 77) |
| SBS55287 | RSDSLLR (SEQ ID NO: 31) | QSSDLRR (SEQ ID NO: 73) | RSDNLSE (SEQ ID NO: 74) | ERANRNS (SEQ ID NO: 75) | RSDNLAR (SEQ ID NO: 76) | QKVNLRE (SEQ ID NO: 78) |
| SBS53855 | TMHQRVE (SEQ ID NO: 62) | TSGHLSR (SEQ ID NO: 63) | RSDTLSQ (SEQ ID NO: 79) | DRSDLSR (SEQ ID NO: 40) | QKATRTT (SEQ ID NO: 70) | RNASRTR (SEQ ID NO: 72) |
| SBS52774 | RKQTRTT (SEQ ID NO: 80) | HRSSLRR (SEQ ID NO: 81) | RSDHLST (SEQ ID NO: 47) | TSANLSR (SEQ ID NO: 82) | RSDNLSE (SEQ ID NO: 74) | WHSSLRV (SEQ ID NO: 83) |
| SBS53909 | RSAHLSR (SEQ ID NO: 84) | DRSDLSR (SEQ ID NO: 40) | RSDVLSV (SEQ ID NO: 85) | QNNHRIT (SEQ ID NO: 86) | RSDVLSE (SEQ ID NO: 60) | SPSSRRT (SEQ ID NO: 87) |
| SBS52742 | RSAHLSR (SEQ ID NO: 84) | DRSDLSR (SEQ ID NO: 40) | RSDSLSV (SEQ ID NO: 88) | QNANRKT (SEQ ID NO: 89) | RSDVLSE (SEQ ID NO: 60) | SPSSRRT (SEQ ID NO: 87) |
| SBS53856 | TMHQRVE (SEQ ID NO: 62) | TSGHLSR (SEQ ID NO: 63) | RSDSLST (SEQ ID NO: 90) | DRANRIK (SEQ ID NO: 91) | QKATRTT (SEQ ID NO: 70) | RNASRTR (SEQ ID NO: 72). |

2. An isolated cell comprising the fusion molecule of claim 1.

3. The cell of claim 2, further comprising an inactivated beta 2 microglobulin (B2M), PD1 and/or CTLA4 gene.

4. The cell of claim 2, further comprising a transgene encoding a chimeric antigen receptor (CAR), a transgene encoding an Antibody-coupled T-cell Receptor (ACTR) and/or a transgene encoding an engineered TCR.

5. The cell of claim 2, wherein the cell is a lymphoid cell, a stem cell, or a progenitor cell.

6. The cell of claim 4, wherein the cell is a T-cell, an induced pluripotent stem cell (iPSC), an embryonic stem cell, a mesenchymal stem cell (MSC), or a hematopoietic stem cell (HSC).

7. A pharmaceutical composition comprising the cell according to claim 2.

8. A polynucleotide encoding the fusion molecule of claim 1.

9. The polynucleotide of claim 8, wherein the polynucleotide is a viral vector, a plasmid or mRNA.

10. A method of treating a cancer, the method comprising introducing the cell according to claim 2 to a subject with cancer.

11. The pharmaceutical composition of claim 7, further comprising a genetically modified cell descended from the cell of claim 1.

* * * * *

UNITED STATES PATENT AND TRADEMARK OFFICE
CERTIFICATE OF CORRECTION

PATENT NO. : 11,352,631 B2
APPLICATION NO. : 15/380643
DATED : June 7, 2022
INVENTOR(S) : Gary K. Lee, David Paschon and Lei Zhang It is certified that error appears in the above-identified patent and that said Letters Patent is hereby corrected as shown below:

In the Claims

Column 95, Claim 1, Row 8 (after the row that starts with SBS55287 and before the row that starts with SBS52774) should read:

| SBS53885 | RSDTLSE (SEQ ID NO:79) | TSGSLTR (SEQ ID NO:37) | RSDHLST (SEQ ID NO:47) | TSSNRTK (SEQ ID NO:71) | RSDNLSE (SEQ ID NO:74) | WHSSLRV (SEQ ID NO:83) |
|---|---|---|---|---|---|---|

Column 96, Claim 11, Line 54 should read:
cell of claim 2.

Signed and Sealed this
Third Day of January, 2023

Katherine Kelly Vidal
*Director of the United States Patent and Trademark Office*